US012767958B2

(12) United States Patent
Greco et al.

(10) Patent No.: US 12,767,958 B2
(45) Date of Patent: Oct. 20, 2026

(54) HYBRID FORMULATION OF RESPONSIVE POLYMERIC NANOCARRIERS FOR THERAPEUTIC AND DIAGNOSTIC DELIVERY

(71) Applicants: Chad Greco, Newark, DE (US); Thomas Epps, III, Bear, DE (US); Millicent Sullivan, Wilmington, DE (US)

(72) Inventors: Chad Greco, Newark, DE (US); Thomas Epps, III, Bear, DE (US); Millicent Sullivan, Wilmington, DE (US)

(73) Assignee: University of Delaware, Newark, DE (US)

( * ) Notice: Subject to any disclaimer, the term of this patent is extended or adjusted under 35 U.S.C. 154(b) by 1004 days.

(21) Appl. No.: 16/316,375

(22) PCT Filed: Jul. 14, 2017

(86) PCT No.: PCT/US2017/042188
§ 371 (c)(1),
(2) Date: Jan. 9, 2019

(87) PCT Pub. No.: WO2018/013957
PCT Pub. Date: Jan. 18, 2018

(65) Prior Publication Data

US 2020/0181649 A1 Jun. 11, 2020

Related U.S. Application Data

(60) Provisional application No. 62/362,085, filed on Jul. 14, 2016.

(51) Int. Cl.

| | |
|---|---|
| ***A61K 9/1272*** | (2025.01) |
| ***A61K 47/00*** | (2006.01) |
| ***C12N 15/11*** | (2006.01) |
| ***C12N 15/88*** | (2006.01) |
| *A61K 41/00* | (2020.01) |
| *A61K 49/00* | (2006.01) |
| *B82Y 5/00* | (2011.01) |

(52) U.S. Cl.
CPC ............ *C12N 15/88* (2013.01); *A61K 9/1272* (2013.01); *C12N 15/111* (2013.01); *A61K 41/00* (2013.01); *A61K 49/0002* (2013.01); *B82Y 5/00* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 5,401,512 | A | 3/1995 | Rhodes et al. |
| 2008/0102127 | A1 | 5/2008 | Gao et al. |
| 2009/0093551 | A1 | 4/2009 | Bhatia et al. |
| 2009/0226528 | A1 | 9/2009 | Czech et al. |
| 2013/0209476 | A1 | 8/2013 | Brenner et al. |
| 2013/0315831 | A1 | 11/2013 | Shi et al. |
| 2015/0283254 | A1 | 10/2015 | Duvall et al. |
| 2016/0022843 | A1 | 1/2016 | Mao et al. |
| 2016/0151482 | A1 | 6/2016 | Carnes et al. |

FOREIGN PATENT DOCUMENTS

| | | | |
|---|---|---|---|
| CN | 102604007 | B | 1/2014 |
| WO | 2008/154482 | A2 | 12/2008 |
| WO | 2014/036194 | A1 | 3/2014 |
| WO | 2016/065306 | A1 | 4/2016 |

OTHER PUBLICATIONS

Jain et al., Mol. Pharmaceutics, 2013, 10: 2416-2425.*
Kozielski et al., ACS Nano, 2014, 8: 3232-3241.*
Liao et al., Biomaterials, 2010, 31: 8780-8799.*
Bekale et al., Colloids and Surfaces B: Biointerfaces, online Dec. 2014, 125: 309-317,.*
Bartlett et al., Nucl. Acids Res., 2006, 34: 322-333.*
Schroeder et al., J. Int. Med., 2009, 267: 9-21.*
Weijzen, Nature Medicine, 2002, 8: 979-986.*
International Preliminary Report on Patentability and Written Opinion for International Application No. PCT/US2017/042188, issued Jan. 15, 2019, 11 pages.
Foster et al., Advanced Healthcare Materials, 4(5):760-70 (2015).
Greco et al., ACS Biomaterials Science & Engineering, pp. A-M (2016).
Green et al., Polym. Chem., 5:5535-41 (2014).
International Search Report for PCT Application No. PCT/US2017/042188, mailed Oct. 2, 2017 by Blaine R. Copenheaver.
Kearney and Skaat, Advanced Healthcare Materials, 4(11):1634-39 (2015).
Perlman, R., "Mouse models of human disease—An evolutionary perspective", Evolution, Medicine, and Public Health[2016], pp. 170-176.
Seok, J., et al. "Genomic responses in mouse models poorly mimic human inflammatory diseases", PNAS, vol. 110, No. 9, Feb. 26, 2013, pp. 3507-3512.

(Continued)

*Primary Examiner* — Ileana Popa
(74) *Attorney, Agent, or Firm* — Buchanan Ingersoll & Rooney PC

(57) ABSTRACT

The present invention provides a nanocomplex comprising at least one agent and a nanocarrier. The agent is bound to the nanocarrier. The nanocarrier comprises at least one cationic polymer responsive to a stimulus, at least one anionic polymer and at least one lipid. The agent is capable of being released from the nanocarrier upon exposure to the stimulus. The released agent is active. The nanocomplex may be used to deliver the agent into cells, in which the agent may be released from the nanocarrier upon exposure of the cells to the stimulus.

18 Claims, 9 Drawing Sheets

Specification includes a Sequence Listing.

(56) References Cited

OTHER PUBLICATIONS

Uhl, E., et al. "Mouse Models as Predictors of Human Responses: Evolutionary Medicine", Curr Pathobiol Rep (2015), 3:219-223.

Han, L., et al., "Effect of binding affinity for siRNA on the in vivo antitumor efficacy of polyplexes", Biomaterials 34 (2013) 5317-5327.

* cited by examiner

HYBRID FORMULATION OF RESPONSIVE POLYMERIC NANOCARRIERS FOR THERAPEUTIC AND DIAGNOSTIC DELIVERY

CROSS-REFERENCE TO RELATED APPLICATION

This application is a U.S. national phase application of International Application No. PCT/US2017/042188, filled Jul. 14, 2017, claiming the benefit of U.S. Provisional Application No. 62/362,085 filed Jul. 14, 2016, the contents of which are incorporated herein by reference in their entireties for all purposes.

REFERENCE TO U.S. GOVERNMENT SUPPORT

This work is supported by a grant from the National Institutes of Health (NIH) Grant No. U54-GM104941. The United States has certain rights in the invention.

FIELD OF THE INVENTION

The invention relates generally to responsive polymeric nanocarriers for therapeutic and diagnostic delivery.

BACKGROUND OF THE INVENTION

Nanocarriers have been used widely for delivery of various active agents into cells for different applications such as therapeutic treatment or diagnosis. To prevent nuclease-mediated degradation of nucleic acids during delivery into cells by cationic nanocarriers, photo-cleavable cationic diblock copolymers have been reported as a potential platform for nucleic acid delivery and light-mediated activation of siRNA release in the diblock copolymer assemblies for controlled gene silence. (Green et al., *Polym. Chem.* 2014, 5, 5535; Foster et al., *Adv. Healthcare Mater.* 2015, 4, 760). However, the current nanocarrier delivery systems for payloads such as nucleic acids, proteins, peptides, small molecules, gold participles, quantum dots, dyes and MRI contrast agents lack the ability to precisely tune the release of the payloads (e.g., siRNA) to maximize biological effects (e.g., gene silencing) of the released payloads in a spatiotemporal manner. There remains a need for nanostructures for stable delivery and highly tunable release of active agents in multiple cell types, especially human primary cells.

SUMMARY OF THE INVENTION

The present invention relates to nanocomplexes and their uses and preparation. A nanocomplex comprising at least one agent and a nanocarrier is provided. The agent is bound to the nanocarrier. The nanocarrier comprises at least one cationic polymer responsive to a stimulus, at least one anionic polymer and at least one lipid. The agent is capable of being released from the nanocarrier upon exposure to the stimulus. The released agent is active.

The agent in the nanocomplex may be a therapeutic agent. The agent may be a diagnostic agent. The agent may be selected from the group consisting of polynucleotides, peptides, proteins, vaccines, small molecule drugs, nanoparticles, contrast agents, and dyes. The polynucleotides may be selected from the group consisting of plasmid DNA (pDNA), complementary DNA (cDNA), small interfering RNA (siRNA), messenger RNA (mRNA), microRNA (miRNA), small hairpin RNA (shRNA), peptide nucleic acid (PNA), locked nucleic acid (LNA), glycol nucleic acid (GNA), and combinations thereof. The proteins may be selected from the group consisting of monoclonal antibodies, polyclonal antibodies, and combinations thereof. The proteins may be enzymes. The proteins may be growth factors. The nanoparticles may comprise gold, silver, quantum dots, iron oxide, or combinations thereof. The nanoparticles may be metallic. The nanoparticles may be non-metallic. The contrast agents may be selected from the group consisting of MRI contrast agents, radiocontrast agents, and combinations thereof.

The stimulus may be selected from the group consisting of light, pH, temperature, ultrasound, enzymes, redox potential, magnetic fields, electric fields, nucleic acids, hydrolysis, mechanical, and combinations thereof. When the stimulus is light, the cationic polymer may comprise mPEG-b-poly(5-(3-(amino)propoxy)-2-nitrobenzyl methacrylate) [mPEG-b-P(APNBMA)]. mPEG is methoxy-poly(ethylene glycol). The mPEG-b-P(APNBMA) may be selected from the group consisting of mPEG-b-P(APNBMA))$_{7.9}$, mPEG-b-P(APNBMA))$_{23.6}$ and a combination thereof.

The anionic polymer in the nanocomplex may be selected from the group consisting of poly(acrylic acid) (PAA), heparin, polyglutamic acid (γ-PGA), and polynucleotides. The anionic polynucleotides may be selected from the group consisting of plasmid DNA (pDNA), complementary DNA (cDNA), small interfering RNA (siRNA), messenger RNA (mRNA), microRNA (miRNA), small hairpin RNA (shRNA), locked nucleic acid (LNA), glycol nucleic acid (GNA), and combinations thereof. The anionic polymer may comprise anionic copolymers based on methacrylic acid and methyl methacrylate having a ratio of the free carboxyl groups to the ester groups at 1.2.

The lipid in the nanocomplex may be selected from the group consisting of N-[1-(2,3-dioleyloxy)propyl]-N,N,N-trimethylammonium chloride (DOTMA), 1,2-bis(oleoyloxy)-3-(trimethylammonio)propane (DOTAP), 2,3-dioleyloxy-N-[2(sperminecarboxamido)ethyl]-N,N-dimethyl-I-propanaminium, trifluoroacetate (DOSPA), dioleoylphosphatidylethanolamine (DOPE), dioleoylphosphatidylcholine (DOPC) and a combination thereof.

In some embodiments of the nanocomplex, the agent comprises at least one small interfering RNA (siRNA), the stimulus is light, the cationic polymer consists of mPEG-b-P(APNBMA))$_{7.9}$, mPEG-b-P(APNBMA))$_{23.6}$ or a combination thereof, and the anionic polymer consists of poly (acrylic acid) (PAA) having a molecular weight (MW) of 250 kDa. The siRNA may comprise anti-interleukin 1β (IL1β) siRNA, anti-cadherin 11 (CDH11) siRNA, or a combination thereof. The siRNA may comprise IL1β siRNA. The siRNA may comprise IL1β siRNA and CDH11 siRNA.

The nanocomplex may have a diameter of 1-500 nm.

A composition comprising the nanocomplex according to the present the invention is provided. The agent may remain bound to the nanocarrier for at least one week in the absence of the stimulus. The composition may further comprise a serum protein. The composition may further comprise a bodily fluid. The bodily fluid may be selected from the group consisting of blood, mucus, perspiration, saliva, semen, vaginal fluid, and urine. The bodily fluid may be serum. The agent may remain bound to the nanocarrier at a temperature of 4-40° C. for at least one week.

A method of delivering at least one active agent into cells is provided. The method comprises (a) administering to the cells a composition comprising a nanocomplex according to the present invention. The nanocomplex comprises the agent and a nanocarrier. The agent is bound to the nanocarrier. The nanocarrier comprises at least one cationic polymer responsive to a stimulus, at least one anionic polymer, and at least one lipid. The agent is capable of being released from the nanocarrier upon exposure to the stimulus, and the released agent is active. As such, the nanocomplex moves into the cells. The agent remains bound to the nanocarrier in the cells until the cells are exposed to the stimulus. The agent may remain bound to the nanocarrier in the cells for at least one week in the absence of the stimulus.

The method may further comprise (b) exposing the cells to the stimulus such that the agent is released from the nanocarrier and the released agent is active. The method may further comprise repeating step (a) for at least once before step (b). When the agent comprises a polynucleotide having a nucleotide sequence encoding a protein, the method may further comprise expressing the protein in the cells after step (b).

When the cells express at least one protein and the agent comprises at least one small interfering RNA (siRNA) against the protein, the method may further comprise reducing the expression of the protein. The protein may comprise IL1β. The protein may further comprise CDH11. When the cells are fibroblasts, the method may further comprise altering differentiation of the cells. When the cells are fibroblasts, the method may further comprise altering proliferation of the cells. When the cells are fibroblasts, the method may further comprise altering cell-cell interactions of the cells. The fibroblasts may be human aortic adventitial fibroblasts (AoAFs).

According to the method of the present invention, the cells may be human primary cells. The cells may be from a subject. The cells may be in a subject.

DETAILED DESCRIPTION OF THE INVENTION

Figure 1:
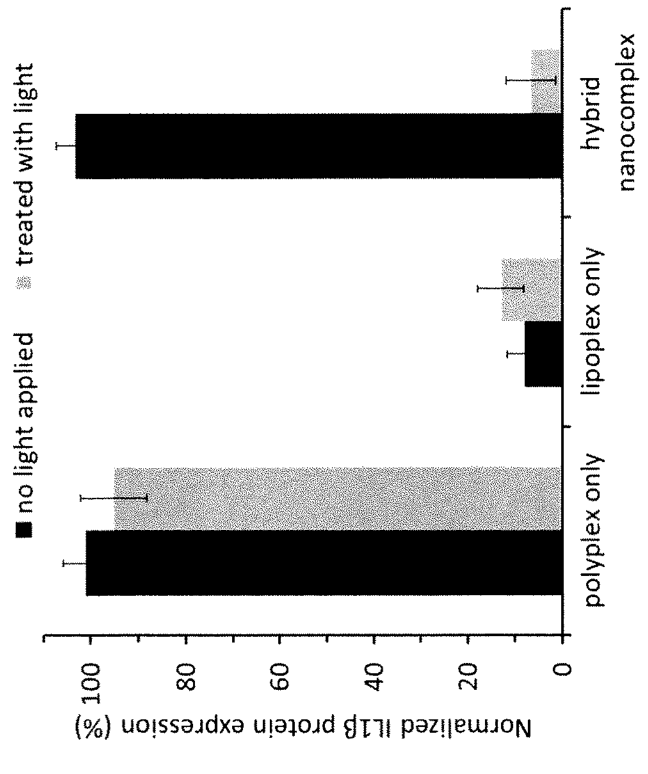
FIG. 1 shows photo-controlled IL1β protein silencing with mPEG-b-P(APNBMA) polyplexes, LIPOFECTAMINE RNAiMAX lipoplexes, and hybrid nanocomplexes. AoAFs were treated with siRNA using the various carriers, irradiated with 365 nm light for either 0 min (black bars) or 10 min (gray bars), and lysed for western blot analysis at 48 h post-transfection. Data represent the IL1β protein expression levels relative to the levels of the loading control glyceraldehyde 3-phosphate dehydrogenase (GAPDH), normalized to the protein levels in controls with no siRNA treatment. Results are shown as the mean±standard deviation of data obtained from three independent experiments.

The present invention provides new nanocarriers comprising responsive cationic polymers, anionic polymers, and lipids and the uses of the nanocarriers for delivery of active agents, including therapeutic agents (e.g., nucleic acids, charged proteins/peptides, charged small molecules) and diagnostic agents (e.g., gold nanoparticles, quantum dots, dyes, MRI contrast agents). The active agents are bound to the nanocarriers to form very stable nanocomplexes, which remain dormant until triggered by a stimulus to release the active agents from the nanocarrier, leading to tunable release and robust biological responses (e.g., gene silencing or gene expression) in multiple cell types, especially human primary cells. Given the ease of preparation, versatility of composition, and precisely tuned stimulus-triggered response, the nanocomplexes allow for delivery of numerous active agents in a wide range of biomedical applications. Furthermore, the modular design of these nanocomplexes allows variations of each component, some of which may contain other functional moieties, to be incorporated into the nanocarrier to tailor the behavior for each nanocarrier system.

The term "polymer" used herein refers to a substance made of a chemical compound, a biological molecule, or a combination thereof that consists of many subunits comprised of one or more atoms (or groups of atoms) that are linked together.

The invention provides a nanocomplex comprising an agent and a nanocarrier. The nanocarrier comprises at least one cationic polymer responsive to a stimulus, at least one anionic polymer and at least one lipid. The agent is capable of being released from the nanocarrier upon exposure to the stimulus and is active after being released from the nanocarrier.

The nanocomplex may have a diameter in the range of about 1-1,000 nm, 1-750 nm, 1-500 nm, 1-250 nm or 100-250 nm.

The nanocomplex may be prepared by mixing the agent with the nanocarrier under suitable conditions. The formation of the nanocomplex may be spontaneously self-assembled through interaction between the agent and the nanocarrier, directly or indirectly via a linker, which may be a chemical compound, a biological molecule or a combination thereof.

The nanocarrier may be prepared by mixing the stimulus responsive cationic polymer, the anionic polymer and the lipid under suitable conditions. The formation of the nanocarrier may be spontaneously self-assembled through interaction among the stimulus responsive cationic polymer, the anionic polymer and the lipid, directly or indirectly via one or more linkers, each of which may be a chemical compound, a biological molecule or a combination thereof.

The nanocarrier and the nanocomplex may be formed simultaneously after mixing the agent, the stimulus responsive cationic polymer, the anionic polymer and the lipid under suitable conditions.

The agent may be a chemical compound, a biological molecule or a combination thereof. The agent may be bound to one or more nanocarrier components through noncovalent interactions. The agent may be charged.

The agent may be a therapeutic agent, for example, a polynucleotide, a peptide, a protein, a vaccine or a small molecule drug. The polynucleotide as the agent may be a plasmid DNA (pDNA), a complementary DNA (cDNA), a small interfering RNA (siRNA), a messenger RNA (mRNA), a microRNA (miRNA), a small hairpin RNA (shRNA), a peptide nucleic acid (PNA), a locked nucleic acid (LNA), a glycol nucleic acid (GNA), or a combination thereof. The polynucleotide as the agent may comprise a nucleotide sequence that encodes for a protein under control of a promoter, for example, an inducible promoter. The protein as the agent may be selected from the group consisting of monoclonal antibodies, polyclonal antibodies, and combinations thereof. The protein as the agent may be an enzyme.

The agent may be a diagnostic agent, for example, a nanoparticle, a contrast agent, or a dye. The nanoparticle may be metallic or non-metallic. The nanoparticle may comprise gold, silver, a quantum dot, iron oxide, or a combination thereof. The contrast agent may be selected from the group consisting of MRI contrast agents, radiocontrast agents, and combinations thereof.

The cationic polymer may be selected to be responsive to a specific stimulus. When the stimulus is light, the cationic polymer may comprise mPEG-b-P(APNBMA). The mPEG-b-P(APNBMA) may be mPEG-b-P(APNBMA))$_{7.9}$, mPEG-b-P(APNBMA))$_{23.6}$ or a combination thereof. mPEG-b-P(APNBMA))$_{7.9}$ and mPEG-b-P(APNBMA))$_{23.6}$ may be combined at a molar ratio of about 0-100, for example, about 1:1.

The anionic polymer may be selected based on its affinity to a charged agent. For example, the anionic polymer may be poly(acrylic acid) (PAA), heparin, polyglutamic acid (γ-PGA), or a polynucleotide. The anionic polynucleotide may be a plasmid DNA (pDNA), a complementary DNA (cDNA), a small interfering RNA (siRNA), a messenger RNA (mRNA), a microRNA (miRNA), a small hairpin RNA (shRNA), a locked nucleic acid (LNA), a glycol nucleic acid (GNA), or a combination thereof. The anionic polymer may comprise anionic copolymers based on methacrylic acid and methyl methacrylate having a ratio of free carboxyl groups to ester groups, for example, about 1.2.

The lipid may be selected based on its tendency to interact with a specific cell type or multiple cell types. Examples of suitable lipids include N-[1-(2,3-dioleyloxy)propyl]-N,N,N-trimethylammonium chloride (DOTMA), 1,2-bis(oleoyloxy)-3-(trimethylammonio)propane (DOTAP), 2,3-dioleyloxy-N-[2(sperminecarboxamido)ethyl]-N,N-dimethyl-I-propanaminium, trifluoroacetate (DOSPA), dioleoylphosphatidylethanolamine (DOPE), dioleoylphosphatidylcholine (DOPC) and combinations thereof.

In some embodiments of the nanocomplexes, the agent comprises at least one small interfering RNA (siRNA), the stimulus is light, the cationic polymer consists of mPEG-b-P(APNBMA))$_{7.9}$, mPEG-b-P(APNBMA))$_{23.6}$ or a combination thereof, and the anionic polymer consists of PAA having a molecular weight (MW) of about 250 kDa. The lipid may be LIPOFECTAMINE RNAiMAX transfection reagent. The siRNA may comprise anti-interleukin 1β (IL1β) siRNA, anti-cadherin 11 (CDH11) siRNA, or a combination thereof.

The stimulus may be a physical or chemical stimulus. For example, the stimulus may be light, pH, temperature, ultrasound, enzymes, redox potential, magnetic fields, electric fields, nucleic acids, hydrolysis, mechanical, or a combination thereof.

In the absence of the stimulus, at least about 50, 60, 70, 80, 90, 95, or 99 wt % of the agent may remain bound to the nanocarrier, for example, at a predetermined temperature, for example, about 0-50° C., 4-40° C. or 25-40° C., and/or for a predetermined period of time, for example, at least about 1, 2, 3, 4, 5, 6 or 7 days, 1, 2 or 4 weeks, or 1, 2, 3, 6, or 12 months. The amount of the agent that remains bound to the nanocarrier could be modified by variations in the molecular weight or ratios of the components of the nanocomplex, or by inclusion of specific anionic polymers, particles, or lipids as components in the nanocomplex.

Upon exposure to the stimulus, at least about 50, 60, 70, 80, 90, 95, or 99 wt % of the agent may be released from the nanocarrier, for example, at a predetermined temperature, for example, about 0-50° C., 4-40° C. or 25-40° C., and/or within a predetermined period of time, for example, about 5, 10, 30 or 60 seconds, 5, 10, 15, 30 or 60 minutes, or 2, 5, 12, 18 or 24 hours. The amount of the agent that is released from the nanocarrier could be modified by variations in the molecular weight or ratios of the components of the nanocomplex, or by inclusion of specific anionic polymers, particles, or lipids as components in the nanocomplex.

For each nanocomplex of the present invention, a composition comprising the nanocomplex is provided. The composition may further comprise a suitable carrier, diluent or excipient. In the absence of the stimulus, at least about 50, 60, 70, 80, 90, 95, or 99 wt % of the agent may remain bound to the nanocarrier, for example, at a predetermined temperature, for example, about 0-50° C., 4-40° C. or 25-40° C., and/or for a predetermined period of time, for example, for at least about 1, 2, 3, 4, 5, 6 or 7 days, 1, 2 or 4 weeks, or 1, 2, 3, 6, or 12 months. Upon exposure to the stimulus, at least about 50, 60, 70, 80, 90, 95, or 99 wt % of the agent may be released from the nanocarrier, for example, at a predetermined temperature, for example, about 0-50° C., 4-40° C. or 25-40° C., and/or within a predetermined period of time, for example, within about 5, 10, 30 or 60 seconds, 5, 10, 15, 30 or 60 minutes, or 2, 5, 12, 18 or 24 hours.

The composition may further comprise a serum protein. Examples of serum proteins include albumins, immunoglobulins, fibrinogen, fibronectin, vitronectin, or lipoproteins. Where a serum protein is present in the composition, at least about 50, 60, 70, 80, 90, 95, or 99 wt % of the agent may remain bound to the nanocarrier at a temperature of 4-40° C. for at least one week in the absence of the stimulus.

The composition may further comprise a bodily fluid. The bodily fluid may be selected from the group consisting of blood, mucus, perspiration, saliva, semen, vaginal fluid, and urine. In one embodiment, the bodily fluid is serum.

A method of delivering an active agent into cells is provided. The method comprises administering to the cells a composition comprising the nanocomplex of the present invention such that the nanocomplex moves into the cells. The nanocomplex comprises the agent and a nanocarrier. The agent is bound to the nanocarrier. The nanocarrier comprises at least one cationic polymer responsive to a stimulus, at least one anionic polymer, and at least one lipid.

The agent is capable of being released from the nanocarrier upon exposure to the stimulus, and the agent released from the nanocarrier is active. The agent remains bound to the nanocarrier until triggered by the stimulus. The agent may be charged.

According to the delivery method, in the absence of the stimulus, at least about 50, 60, 70, 80, 90, 95, or 99 wt % of the agent in the cells may remain bound to the nanocarrier at a predetermined temperature, for example, about 0-50° C., 4-40° C. or 25-40° C., for a predetermined period of time, for example, for at least about 1, 2, 3, 4, 5, 6 or 7 days, 1, 2 or 4 weeks, or 1, 2, 3, 6, or 12 months.

The cells may be any types of cells in or from a subject. The subject may be a mammal, for example, a mouse or human. The cells may be human cells, for example, human primary cells.

The delivery method may further comprise exposing the cells to the stimulus such that the agent is released from the nanocarrier. The agent released from the nanocarrier is active. Before exposing the cells to the stimulus, the composition comprising the nanocomplex may be administered to the cells for another one, two, three or more times. Upon exposure to the stimulus, at least about 50, 60, 70, 80, 90, 95, or 99 wt % of the agent in the cells may be released from the nanocarrier, for example, at a predetermined temperature, for example, about 0-50° C., 4-40° C. or 25-40° C., and/or within a predetermined period of time, for example, within about 5, 10, 30 or 60 seconds, 5, 10, 15, 30 or 60 minutes, or 2, 5, 12, 18 or 24 hours.

Where the agent comprises a polynucleotide having a nucleotide sequence encoding a protein, the delivery method may further comprise expressing the protein in the cells after the exposure.

Where the cells express at least one protein and the agent comprises at least one small interfering RNA (siRNA) against the protein, the delivery method may further comprise reducing the expression of the protein. Where the cells express interleukin 1β (IL1β) and/or cadherin 11 (CDH11), the delivery method further comprises reducing the expression of IL1β and/or CDH11. Where the cells are fibroblasts expressing IL1β and/or CDH11, the delivery method further comprises altering differentiation or proliferation of the cells, or altering cell-cell interactions. The fibroblasts may be human aortic adventitial fibroblasts (AoAFs). The alteration may be attenuation.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

EXAMPLE 1

Attenuation of Maladaptive Responses in Aortic Adventitial Fibroblasts through Stimuli-Triggered siRNA Release from Lipid-Polymer Nanocomplexes Lipid-siRNA assemblies are modified with photo-responsive polymers to enable spatiotemporally-controlled silencing of interleukin 1 beta (IL1β) and cadherin 11 (CDH11), two genes that are essential drivers of maladaptive responses in human aortic adventitial fibroblasts (AoAFs). These hybrid nanocomplexes address the critical challenge of locally mitigating fibrotic actions that lead to the high rates of vascular graft failures. In particular, the lipid-polymer formulations provide potent silencing of IL1β and CDH11 that is precisely modulated by a photo-release stimulus. Moreover, a dynamic modeling framework is used to design a multi-dose siRNA regimen that sustains knockdown of both genes over clinically-relevant timescales. Multi-dose suppression illuminates a cooperative role for IL1β and CDH11 in pathogenic adventitial remodeling and is directly linked to desirable functional outcomes. Specifically, myofibroblast differentiation and cellular proliferation, two of the primary hallmarks of fibrosis, are significantly attenuated by IL1β silencing. Meanwhile, the effects of CDH11 siRNA treatment on differentiation become more pronounced at higher cell densities characteristic of constrictive adventitial remodeling in vivo. Thus, this work offers a unique formulation design for photo-responsive gene suppression in human primary cells and establishes a new dosing method to satisfy the critical need for local attenuation of fibrotic responses in the adventitium surrounding vascular grafts.

1. Introduction

Cardiovascular disease is the leading cause of death worldwide, and vascular reconstructive surgeries, including the placement of bypass grafts, have become routine procedures for treating these ailments. Unfortunately, even standard treatments, such as autologous vein grafts from the leg or arterial grafts from the arm or thorax, commonly fail within a few years due to inappropriate vessel remodeling. These graft failures are primarily driven by maladaptive cellular responses elicited by tissue injury and hemodynamic stress. Anastomoses, the sites of surgical vessel connection, are at particular risk due to suture line scarring, stricture, and higher incidences of stenosis and fibrosis. Although drug eluting stents and externally applied films have shown promise in preventing complications, these interventions provide inadequate spatial and temporal control over cell behaviors in the graft conduit. Thus, new methods are needed that can locally target the key cell types involved in failure. Such approaches could enable improved healing responses by tuning the application and release of regulatory therapies according to the localized environment within the site of injury.

Adventitial fibroblasts (AFs), which populate the outermost layer of arteries, are particularly important cellular mediators of normal and pathogenic vessel remodeling. Specifically, AFs are the dominant cell type in the adventitium, and they regulate the structural integrity and growth of blood vessels through the production of extracellular matrix and the recruitment of the microvascular blood supply. AFs contribute to the injury response through a variety of mechanisms, including their capacity to rapidly proliferate and differentiate into myofibroblasts, which have the ability to generate high contractile forces though the expression of alpha smooth muscle actin (αSMA) and the formation of multicellular networks. Although such forces are necessary to induce vessel remodeling, this behavior is detrimental when it becomes excessive following reconstructive surgery. In particular, AF proliferation and differentiation directly control the progression of intimal hyperplasia and fibrosis, leading to the accumulation of fibrous connective tissue, vessel thickening and scarring, and ultimately, graft failure. Therapeutic approaches geared toward the attenuation of AF-driven fibrosis would be extremely valuable. In fact, recent studies show significant promise for modulating adventitial responses through local application of biomaterials, such as hydrogels, to the abluminal surface of skeletonized vessels (e.g., contacting adventitium), a procedure which was shown to reverse a series of adverse vessel remodeling responses to mechanical injury when the materials were applied during the acute inflammatory phase of post-surgical recovery.

In addition to the local targeting of AFs through biomaterials application, the control of genes that regulate maladaptive responses in AFs also is critical to promote healing at anastomotic sites. For example, recent studies have elucidated key proliferative effectors and phenotypic modulators that likely play significant roles in the fibrotic response of AFs. Two prominent genes noted in the above studies are interleukin 1 beta (IL1β), a cytokine that mediates injury-induced inflammation, and cadherin 11 (CDH11), a cell-cell adhesion receptor that coordinates the contraction of fibroblast populations. It also is important to understand the differential effects of IL1β and CDH11 on the signaling cascade initiated by transforming growth factor beta 1 (TGF-β1), a potent activator of myofibroblasts that is produced by local inflammatory cells and overexpressed in diseased environments. Although TGF-β1-induced changes in both IL1β and CDH11 expression have been correlated with myofibroblastic differentiation and inflammation in fibroblastic lineages, the functional relationship between IL1β and CDH11 has not been explored in the context of adventitial remodeling.

Herein, we modified lipid-small interfering RNA (siRNA) complexes (lipoplexes) with stimuli-responsive polymers to gain spatiotemporal control over gene knockdown in human primary aortic adventitial fibroblasts (AoAFs), which enabled the elucidation of the functional roles of IL1β and CDH11 in improving vascular healing. These hybrid nanocomplexes were necessary because primary cells (e.g., AoAFs) tend to be refractory to transfection compared to immortalized cell lines. Moreover, our previous work established other beneficial properties of our mPEG-b-poly(5-(3-(amino)propoxy)-2-nitrobenzyl methacrylate) [mPEG-b-P(APNBMA)] block copolymer system for vascular applications, including high stability and the capacity to locally regulate the extent of protein silencing on cellular length scales. Such features make our nanocomplexes ideal for incorporation into biomaterials, such as abluminally-applied hydrogels, to enable regulation of adventitial cell behavior through a combination of mechanical stimuli and spatial regulation of gene expression in anastomoses. Additionally, the precisely controlled nature of the system allows for accurate predictions of siRNA dosing regimens that facilitate gene knockdown over clinically-relevant timescales associated with adventitial remodeling (one week).

We exploited these characteristics through the formulation of hybrid nanocarriers that mediated on-demand, spatially-controlled knockdown of IL1β and CDH11 in AoAFs to ≤5% of their initial levels following treatment with a photo-stimulus. The silencing of IL1β on its own significantly reduced myofibroblast differentiation and proliferation, whereas CDH11 silencing on its own had only a moderate effect. Subsequently, kinetic modeling approaches were used to design dosing regimens that fully silenced IL1β and/or CDH11 together, over sustained time periods. Complete attenuation of TGF-β1-induced myofibroblast differentiation was achieved by simultaneously silencing IL1β and CDH11 for one week, the timescale relevant to adventitial remodeling. Thus, we uncovered synergistic functional roles of IL1β and CDH11 in AoAFs and showed that sustained knockdown of these genes is a viable method for mitigating fibrotic responses. In the longer term, the photo-sensitive lipid-polymer nanocomplexes offer a unique opportunity to locally regulate fibrotic conditions in anastomoses and improve healing following cardiovascular surgery.

2. Results and Discussion 2.1 Hybrid Nanocomplexes Enable On/Off Control Over Gene Silencing To achieve spatially-tailored and temporally-tuned gene silencing in AoAFs, various formulations of polymer-only-siRNA complexes (polyplexes) were tested that had previously been shown to provide efficient, light-triggered siRNA delivery in murine embryonic fibroblasts. None of the polyplex formulations were able to mediate efficient gene silencing in AoAFs (FIG. 1). We suspected that a lack of endosomal escape might be the limiting factor, based on prior evidence demonstrating that human primary cells often are refractory to transfection. Lipoplexes comprised of LIPOFECTAMINE RNAiMAX were shown to transfect AoAFs efficiently (FIG. 1), presumably because cationic lipids can interact with endosomal membranes and enhance cargo escape in primary cells. However, these lipid solutions were not capable of mediating photo-controlled, spatiotemporal release. In contrast, hybrid nanocomplexes combining lipids and polymers remained dormant in the absence of a photo-trigger but rapidly released siRNA following the application of light, leading to efficient gene silencing in AoAFs (FIG. 1). The model gene, IL1β, was knocked down to ~5% of the protein expression levels measured in untreated controls, demonstrating that the hybrid siRNA nanocarrier system was vital to overcoming the shortcomings of the individual polyplex and lipoplex formulations. Moreover, the on/off control over siRNA activity afforded by the hybrid nanocomplexes can be easily extended to spatially regulate gene expression at cellular length scales using previously described procedures.

Figure 2:
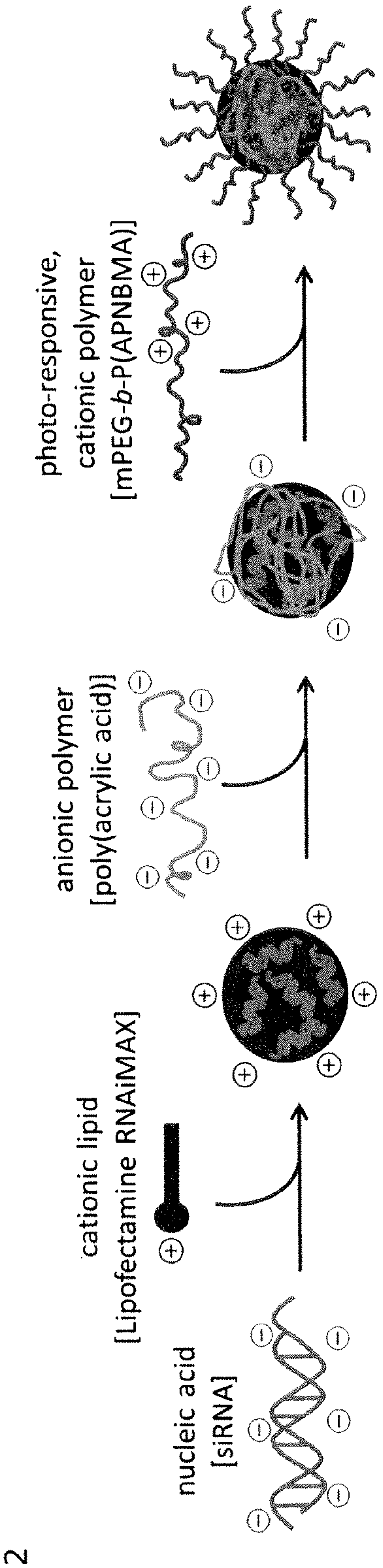
FIG. 2 shows a schematic drawing depicting formulation of hybrid nanocomplexes according to one embodiment of the present invention. First, nucleic acids (siRNA) were encapsulated in lipoplexes using cationic lipid (LIPOFECTAMINE RNAiMAX). Second, anionic polymer (PAA) was added to reverse the lipoplexes surface charge. Third, a mixture of photo-responsive cationic polymers (mPEG-b-P$(APNBMA)_n$ with 50% n=7.9 and 50% n=23.6, on a molar basis of cationic amine groups) was incorporated into the formulation to form the hybrid nanocomplexes.

The hybrid nanocomplexes were formulated according to the process depicted in FIG. 2. First, siRNA was complexed with a cationic lipid, LIPOFECTAMINE RNAiMAX. Because these lipoplexes possessed a net positive charge and the mPEG-b-P(APNBMA) also was cationic, an anionic component was needed to facilitate electrostatic interactions. Poly(acrylic acid) [PAA], a polymer with a high anionic charge density, was mixed with the lipoplexes to reverse the overall charge. Finally, the cationic mPEG-b-P(APNBMA) was incorporated to impart photo-responsive characteristics (charge reversal) to the system.

The structural design and formulation process of the hybrid nanocomplexes share similarities with other lipid-polymer systems in the literature. Generally, polymers are added to lipid-based carriers to impart a specific characteristic to the system. These features include reduced charge, stealthy behavior, biocompatibility, smaller sizes, and enhanced endosomal escape. Although these modifications have proven to be effective, few stimuli-responsive components have been used to induce controlled siRNA release within hybrid lipid-polymer assemblies. Herein, mPEG-b-P(APNBMA) was used to gain photo-responsive control over the disassembly of lipid-containing complexes. This favorable combination of behaviors (e.g., light-responsiveness and endosomal escape) presumably arose as a result of polymer shielding of the endosome-destabilizing cationic lipids prior to light-triggered polymer cleavage/charge reversal, which then initiated lipid-mediated endosome destabilization. Thus, our nanocomplexes provide the benefits of both lipids and stimuli-sensitive polymers, enabling precisely tuned on/off control over nucleic acid activity in human primary AoAFs.

Figure 3:
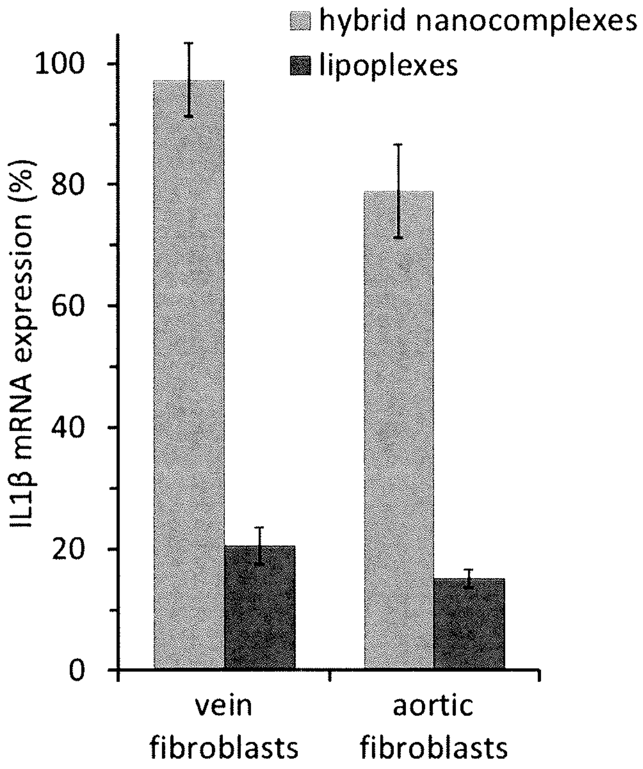
FIG. 3 shows gene silencing efficiencies of hybrid lipid-polymer nanocomplexes and Lipofectamine RNAiMAX lipoplexes in rabbit primary vein and aortic fibroblasts. Quantitative PCR (qPCR) analyses compared the IL1β mRNA expression levels 24 h post-transfection. Results are shown as the mean±standard deviation of data obtained from three independent samples. The hybrid nanocomplexes did not mediate efficient knockdown of IL1β mRNA in rabbit primary vein and aortic fibroblasts, whereas Lipofectamine-only lipoplexes induced significant levels of gene silencing in both cell types. Hybrid nanocomplexes only exhibited efficient gene silencing in human AoAFs (see FIG. 1).

It is important to note that the composition of the nanocomplexes was optimized to transfect human AoAFs. Gene silencing experiments in similar cell types, such as fibroblasts from other species and/or other tissue origins, demonstrated the cell specificity of the nanocomplexes and suggested that the effects of protein knockdown would be minimal in other mesenchymal cells found in adventitium (FIG. 3). The selective transfection of different cell types is a critical potential advantage of our approach. Furthermore, the composition of the multi-component, highly modular hybrid nanocomplex system can be easily tailored to enable improved cell specificity and avoid off-target effects.

2.2 Characterization of Hybrid Nanocomplexes

The hybrid lipid-polymer nanocomplexes were characterized to determine their fundamental physicochemical properties.

TABLE 1

Average size and zeta potential of the hybrid lipid-polymer nanocomplexes based on fluorescence correlation spectroscopy analysis (diameter) and zeta potential analyses.

| | average | standard deviation |
|---|---|---|
| diameter (nm) | 168 | 11 |
| zeta potential (mV) | +3.1 | 2.8 |

As shown in Table 1, the nanocarriers had an average diameter of 168 nm, which is within the size regime of nanoparticles that are able to undergo endocytosis and enter cells. The nanocomplexes had a zeta potential of +3.1 mV (Table 1), indicating that the nanocarrier surface was slightly positively charged but close to neutral. The relatively neutral zeta potential suggests that the mPEG-b-P(APNBMA) polymers were coating the lipoplexes and that the PEG chains were forming an outer corona around the charged cores. The slight positive charge is favorable for inducing cellular uptake while minimizing interactions with serum-components.

Figure 4:
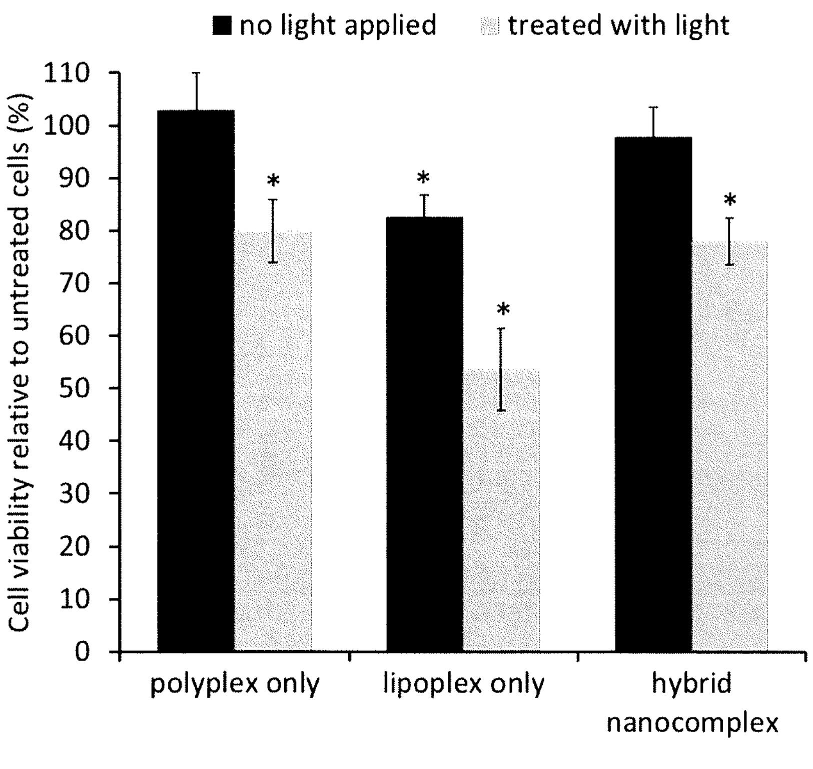
FIG. 4 shows AoAF cell viabilities following treatment with either polyplexes, lipoplexes, or hybrid nanocomplexes with or without 365 nm light irradiation. 48 h following siRNA and light treatment, an Alamar Blue (AB) assay was used to measure cell viability relative to cells that were untreated. Results are reported as the mean±standard deviation of data obtained from three independent experiments. An asterisk indicates a statistically significant difference in cell viability in comparison to the untreated control samples ($p<0.05$). Polymer-only polyplexes and hybrid nanocomplexes exhibited no cytotoxicity, whereas lipid-only lipoplexes and 365 nm light treatment both reduced the cell viability to ~80% relative to untreated controls. The combined effects of lipid-only lipoplexes and 365 nm light treatment further decreased cell viability to ~54%.

Another important consideration in the formulation of new siRNA delivery vehicles is their cytotoxicity, especially when treating sensitive human primary cells such as AoAFs. As shown in previous work, mPEG-b-P(APNBMA)-only polyplexes did not lead to any significant change in cell viability relative to untreated cells (FIG. 4). The hybrid nanocomplexes also possessed excellent biocompatibility (~98% cell viability), similar to the previously-reported polyplexes. AoAFs that were treated with mPEG-b-P(APNBMA)-only polyplexes or the hybrid nanocomplexes combined with the photo-stimulus exhibited a modest (~20%) decrease in cell viability compared to untreated cells, indicating that 365 nm light was moderately cytotoxic. However, lipoplexes comprised of LIPOFECTAMINE RNAiMAX were significantly more cytotoxic than the polyplexes or the hybrid nanocomplexes, as treatment with lipoplexes reduced cell viability by ~18% and ~46% without and with 365 nm light, respectively (FIG. 4). The lack of a significant cytotoxic response of the hybrid lipid-polymer nanocarriers further indicates that the biocompatible mPEG-b-P(APNBMA) forms a corona that shields the cationic lipids from interacting with cells. This shielding feature, and its resulting low cytotoxicity, suggest that the hybrid nanocomplexes hold greater promise for use in therapeutic settings.

Figure 5:
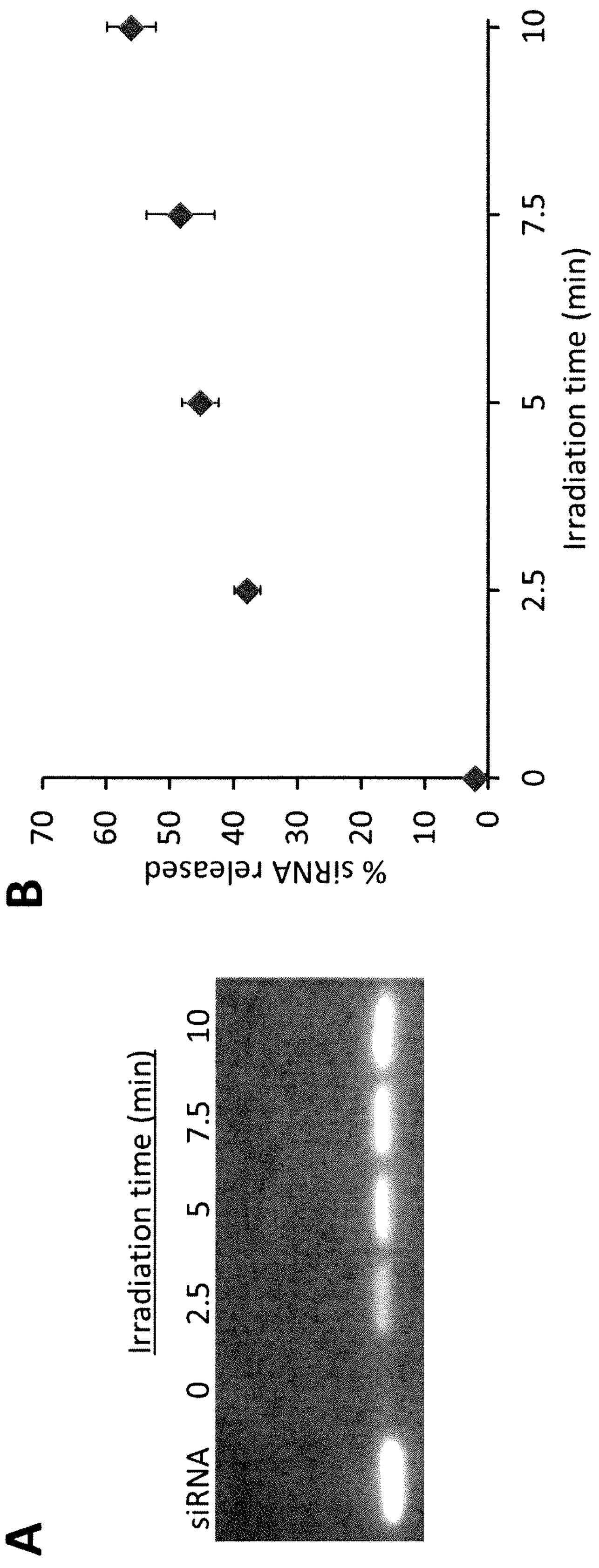
FIG. 5 shows light-triggered siRNA release from hybrid nanocomplexes. The nanocarriers were formulated, incubated in sodium dodecyl sulfate (SDS) solutions at an S/P ratio (S: sulfates on SDS, P: phosphates on siRNA) of 4 to simulate lipid-rich intracellular environments, and irradiated with 365 nm light for various lengths of time. (A) The solutions were analyzed by gel electrophoresis analyses, and (B) the amount of free siRNA was quantified on the basis of relative band intensities via Image) software. Results are reported as the mean±standard deviation of data obtained from three independent experiments. The nanocomplexes encapsulated nearly all the siRNA prior to application of the photo-stimulus. Upon increasing amounts of irradiation with 365 nm light, more siRNA was released.

Finally, the light-triggered siRNA release behavior of the nanocomplexes was explored to gain a better understanding of the on/off gene silencing response. As shown in FIG. 5, nanocarriers that were not irradiated with light remained stable and encapsulated nearly 100% of the siRNA. Nanocomplexes that were treated with the photo-stimulus for increasing lengths of time exhibited increasing amounts of siRNA release. After 10 min of irradiation, which is the dosage of light used during transfections, ~56% of the siRNA was released. The high level of light-triggered siRNA release helps explain the efficient, on/off gene silencing trends detected in cells, even when low concentrations of siRNA (10 nm) were used.

2.3 Gene Silencing Dynamics Following a Single siRNA Dose

Figure 6:
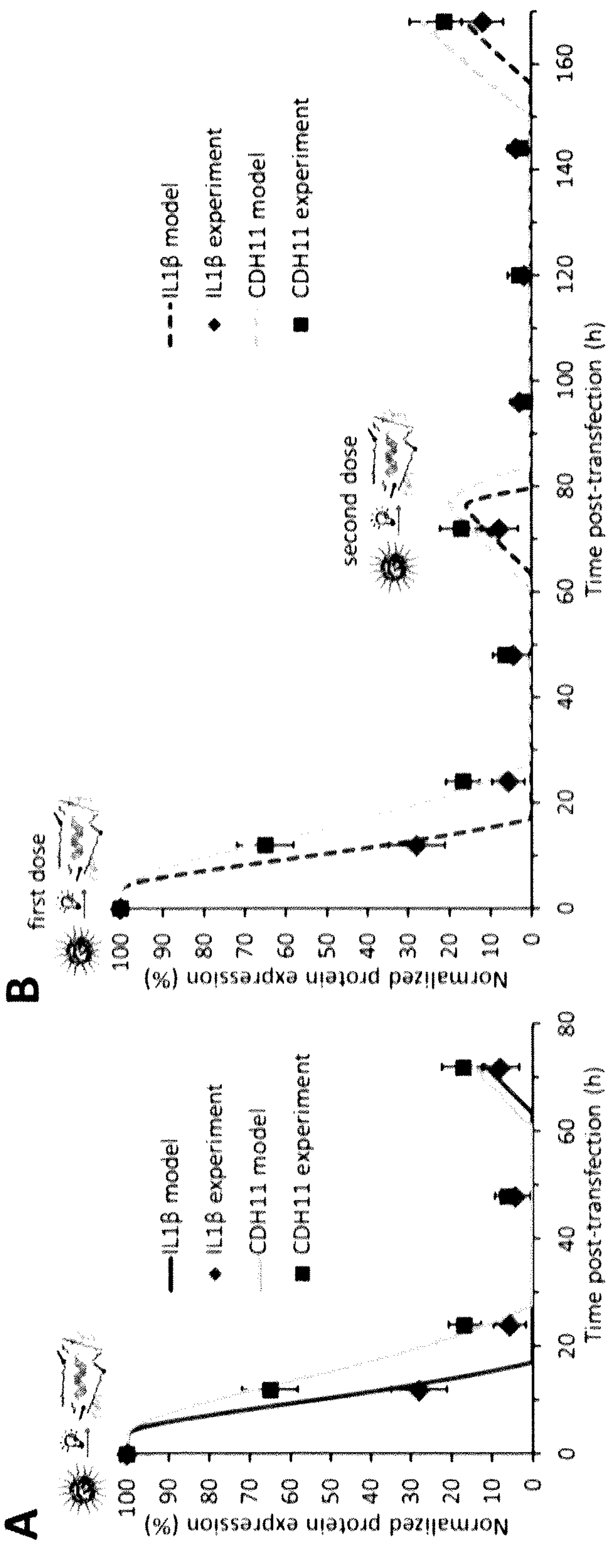
FIG. 6 shows dynamics of IL1β and CDH11 protein silencing following a single dose (A) or double dose (B) of siRNA. Kinetic modeling was used to predict the temporal IL1β (black lines) and CDH11 (gray lines) protein expression following doses of siRNA. Initial protein concentrations were normalized to 100, and the model predictions were verified experimentally using western blotting. Data points represent the normalized IL1β (diamonds) or CDH11 (squares) protein expression levels relative to the loading control. Experimental results are shown as the mean±standard deviation of data obtained from three independent samples. (A) AoAFs were transfected with the hybrid nanocomplexes at t=0 h, irradiated with 365 nm light to release the siRNA 3.5 h post-transfection, and lysed at the times indicated by the data points. (B) AoAFs were transfected with the hybrid nanocomplexes at t=0 h and t=72 h, irradiated with 365 nm light 3.5 h after each transfection, and lysed at the times indicated by the data points.

Given the controlled release nature of the nanocomplexes, the dynamics of protein knockdown were investigated to determine how to appropriately dose siRNA in AoAFs. Two genes implicated in maladaptive responses, IL1β and CDH11, were studied using a combination of experimental analyses and kinetic modeling. siRNAs targeting IL1β or CDH11 were delivered to cells using the nanocomplexes, and siRNA release was induced upon application of a photo-stimulus at 3.5 h post-transfection. According to the model, protein expression for both genes was expected to decrease immediately following photo-induced siRNA release (FIG. 6A). However, the rate of change in protein concentrations varied between the two genes. IL1β protein expression was forecasted to be almost fully knocked down ~16 h post-transfection, whereas complete CDH11 knockdown was not expected until ~27 h post-transfection. The proteins were predicted to be silenced to ≤5% of their initial levels for ~47 h (IL1β) or ~34 h (CDH11) before recovering. Experimental measurements of protein concentrations taken at various times validated these predictions and demonstrated that the model could accurately capture all three phases of the gene silencing process—e.g., initial knockdown, maximal silencing, and recovery of protein expression.

The protein silencing dynamics for IL1β and CDH11 followed the same overall trend, expect that the rate of initial protein knockdown depended on the half-lives of the two proteins (IL1β and CDH11 have protein half-lives of ~2.5 h and ~8 h, respectively). If sufficient amounts of siRNA are released to saturate the RNA-induced silencing complex machinery, the cleavage of targeted mRNAs rapidly occurs, and the translation of new protein is halted. The existing protein, translated before the onset of RNAi initiation, would then degrade in time according to its innate turnover rate. Therefore, the concentration of IL1β should decrease faster than CDH11 on the basis of its shorter protein half-life.

On the other hand, the duration of sustained maximal silencing depends more strongly on the doubling time of the cells, and to a much lesser extent, upon the stability of the siRNA. The intracellular siRNA is diluted in time due both to cell division and degradation from nucleases, and RNAi effects generally only last for a few days in growing cells, such as AoAFs. The concentration of IL1β- and CDH11-targeted siRNA in the AoAFs decreased at approximately the same rate, and the protein levels start to recover at ~3 days post-transfection as detailed by the modeling and experimental data. Thus, these analyses elucidated the dynamics of IL1β and CDH11 knockdown in AoAFs following a single dose of siRNA. These timescales are consistent with those for inflammation-mediated fibroblast proliferation, providing further justification for the use of IL1β- and CDH11-targeted siRNAs for the treatment of cardiovascular disease.

2.4 Gene Silencing Dynamics Following a Double Dose of siRNA

Following severe injury, adventitial remodeling/myofibroblast differentiation occurs over a time period of ~7 days, and thus, sustained gene silencing is needed in such cases. Our kinetic modeling allowed the implementation of dosing schedules that enabled knockdown below a desired threshold over the one week duration. More specifically, using the framework established in FIG. 6A, different dosing regimens were analyzed to predict the RNAi response following a second application of siRNA. As shown in FIG. 6B, the second transfection was started at 72 h; i.e. near the time at which the protein levels were predicted to start recovering after the first transfection. The model forecasted that implementation of this dosing schedule would allow the knockdown of both genes to be sustained for ~7 days at levels of <20% relative to untreated controls. Experimental measurements of protein levels validated this dosing regimen model and demonstrated that the predictions accurately captured the prolonged knockdown and recovery phases. Thus, our modeling approach allowed us to accurately predict that only two doses were needed to achieve gene silencing of both genes over the clinically-relevant timescale of one week. Intriguingly, the relevance of this timescale for modulation of longer-term fibrotic responses was recently demonstrated by Robinson et al., who reported that vessels subjected to common surgical procedures used during grafting (e.g., skeletonization) displayed multiple maladaptive tissue responses within 3 days of surgery, with decreases in cyclic strain stabilizing within ~1 week. In this model, acute abluminal application of thin (~1 mm), mechanically-tunable hydrogels reversed fully many of the adverse responses to surgery. The addition of light-responsive nanocomplexes to such materials could provide a compelling approach to further tune and suppress failure responses, particularly in anastomoses or other regions of the graft tissue experiencing high mechanical stress.

One challenging aspect of implementing predictive siRNA dosing schedules is the effect of the silenced genes on cellular parameters governing responses to subsequent siRNA applications. Proliferation analyses (discussed later) determined that the knockdown of IL1β slowed cellular growth rates by ~30% after each dose. Thus, the kinetic model was updated with this information to account for the change in siRNA dilution rate as a result of a longer cell doubling time. The updated model accurately predicted that IL1β would remain knocked down longer than CDH11, which was verified by experimental measurements. Therefore, the combination of a double dosing regimen and simple kinetic modeling enabled the knockdown of both genes to be sustained for one week in a predictable manner.

2.5 Gene Silencing Affects Myofibroblast Differentiation (αSMA Protein Expression)

One of the primary hallmarks of fibrosis is the differentiation of fibroblasts into myofibroblasts, which is driven by the production of TGF-131 by local inflammatory cells. Accordingly, to simulate the inflammatory fibrotic responses in culture, recombinant TGF-β1 protein was added to the growth medium of AoAFs. The cells were treated with formulations of non-targeted siRNA, IL1β siRNA, CDH11 siRNA, or combined IL1β and CDH11 siRNAs via the single dosing schedule in FIG. 6A. The extent of differentiation was determined by measuring changes in αSMA protein expression, the most widely used indicator of the myofibroblast phenotype. The addition of TGF-β1 induced AoAFs to differentiate into myofibroblasts within 3 days, consistent with responses reported in the literature. Specifically, AoAFs that were not treated with TGF-β1 expressed low levels of αSMA protein relative to F-actin protein; however, cells treated with TGF-β1 and either no siRNA or a single dose of non-targeted siRNA exhibited robust αSMA protein expression.

AoAFs treated with TGF-β1 followed by application of functional siRNAs targeting IL1β exhibited a significant reduction in αSMA staining, indicating that knocking down IL1β blocks the differentiation cascade to a measurable extent. In contrast, TGF-β1-treated cells with silenced CDH11 maintained robust αSMA protein expression. AoAFs that were treated with both IL1β and CDH11 siRNAs also exhibited decreased αSMA staining. The quantification of protein expression based upon these ICC experiments is shown in FIG. 7A and is presented as αSMA relative to F-actin. As can be noted from the micrographs, αSMA protein expression was only significantly attenuated when IL1β was knocked down (either alone or in combination with CDH11) using the single dose regimen.

To determine how myofibroblast differentiation would be affected by the double dosing regimen, αSMA protein expression was analyzed on day 8. The differences in protein expression as a function of IL1β and/or CDH11 knockdown were more prominent in the double dosing experiments, though the overall trends were similar to the single dosing studies (comparison of FIGS. 7A and 7B). The delivery of IL1β siRNA suppressed αSMA levels by ~45% at day 8 relative to treatment with non-targeting siRNA. However, CDH11 silencing alone provided no reduction in αSMA protein expression compared to treatment with non-targeting siRNA. This behavior most likely was exhibited because AoAFs that were treated with only CDH11 siRNA had differentiated to approximately the same extent as cells treated with non-targeting siRNA before application of the second dose (FIG. 7), and further CDH11 knockdown could not reverse the myofibroblast phenotype. A recent report demonstrated that the de-activation of myofibroblasts is difficult to control and that the restricted capacity of myofibroblasts to de-differentiate is a major cause of fibrotic disorders.

Figure 7:
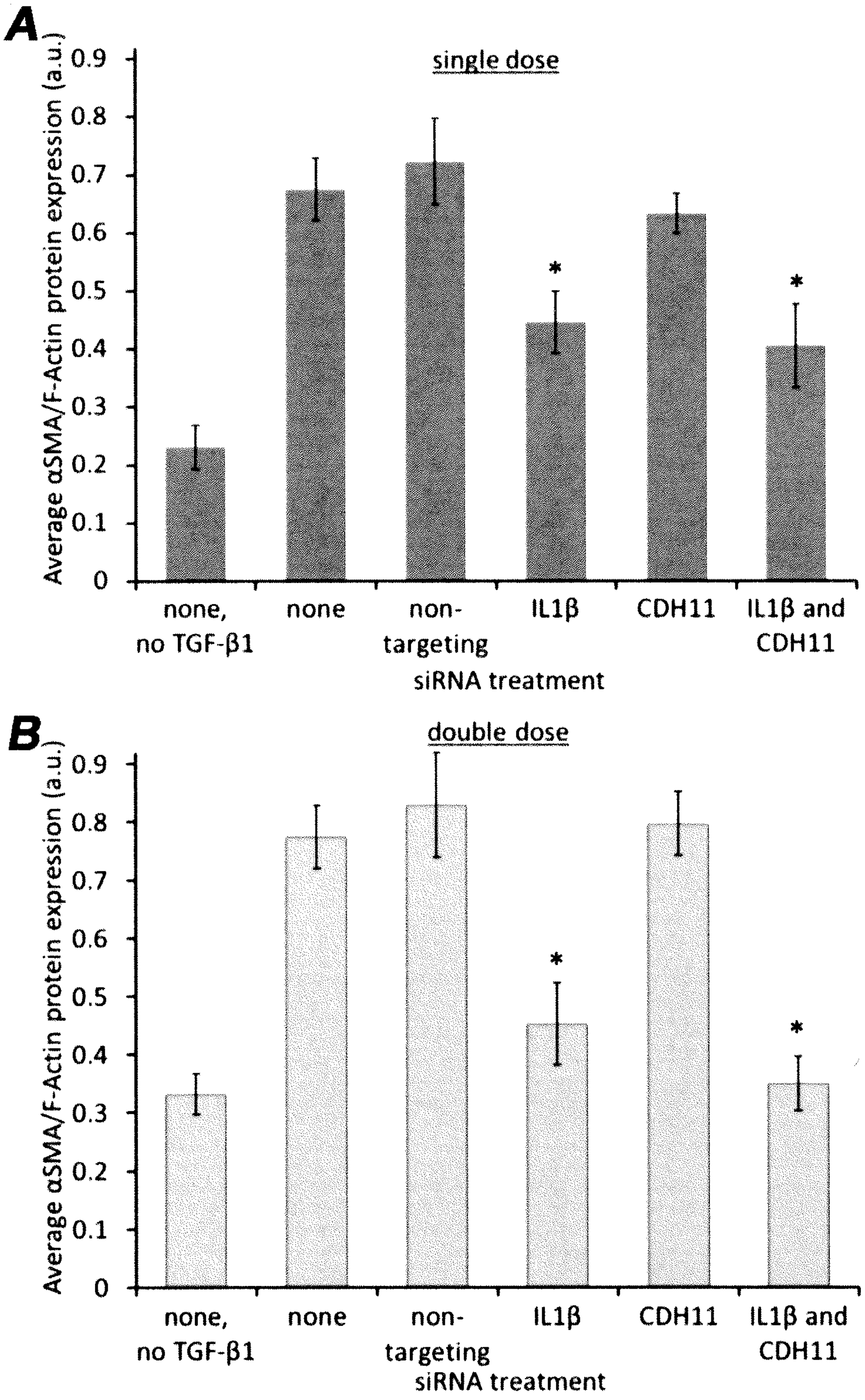
FIG. 7 shows attenuation of myofibroblast differentiation (αSMA protein expression) following siRNA dosing. AoAFs underwent transfection with different siRNA formulations and were treated with either 0 ng $mL^{-1}$ or 10 ng $mL^{-1}$ TGF-β1 to induce differentiation. Quantification of relative αSMA protein expression from single dose Immunocytochemistry (ICC) micrographs in (A). Quantification of relative αSMA protein expression from double dose ICC micrographs, characterized on day 8, in (B). The average total fluorescence intensity of αSMA relative to F-actin of at least 100 cells per sample was measured using ImageJ for both the single and double dose regimens. All results are shown as the mean±standard deviation of data obtained from three independent experiments. An asterisk indicates a statistically significant difference in αSMA protein expression in comparison to the no siRNA and 10 ng $mL^{-1}$ TGF-β1 treatment control ($p<0.05$).

Regardless of dosing regimen, only cells treated with IL1β siRNA exhibited a significant reduction in αSMA protein expression (FIG. 7). In agreement with our findings, Guo et al. (*Arch. Toxicol.* 2013, 87, 1963) demonstrated that the neutralization of IL1β in vivo attenuated fibrosis and was correlated with decreases in TGF-β1 activity. A number of recent studies also reported that increased IL1β levels enhanced the severity of fibrosis in vivo. In a related example, Chen and coworkers (*Exp. Mol. Pathol.* 2009, 87, 189) showed that IL1β-stimulation of HO-8910PM and NIH3T3 cells increased the expression of αSMA and activated proteins involved in myofibroblast differentiation. However, others have reported different impacts of IL1β activity on αSMA expression in other cell types, and moreover, Dewald et al. (*Am. J. Pathol.* 2004, 164, 665) found significant species-specific differences in cellular responses to inflammatory cytokines following myocardial infarction. Our finding that IL1β silencing effectively blocked TGF-β1-induced αSMA protein expression in AoAFs is likely applicable to fibroblasts derived from different organs but may not directly translate to all cell types or species.

CDH11 silencing in AoAFs did not attenuate αSMA protein expression compared to treatment with non-targeting siRNA, and the combination of CDH11 and IL1β silencing also did not further reduce αSMA protein expression as compared with samples treated with IL1β siRNA only (FIG. 7). The knockdown of CDH11 has been shown to regulate the myofibroblast phenotype differently depending on the cell type. For example, Verhoekx et al. (*J. Invest. Dermatol.* 2013, 133, 2664) reported that αSMA expression remained unchanged in human dermal fibroblasts, but was reduced by ~50% in Dupuytren's myofibroblasts following CDH11 silencing. Wang and coworkers (*FASEB J.* 2014, 28, 4551) also found that CDH11 knockdown did not affect differentiation when porcine valvular interstitial cells were treated with 5 ng $mL^{-1}$ of TGF-β1. Moreover, because the activity of CDH11 is dependent on the number of cell-cell contacts, differences in cell density also may contribute to the variations in cellular responses (discussed later).

2.6 Gene Silencing Affects Myofibroblast Differentiation (αSMA mRNA Expression)

To gain a more quantitative understanding of temporal differences in myofibroblast differentiation, changes in the mRNA transcript levels also were analyzed. As shown in FIG. 5A, the trends for the single dosing regimen were generally in agreement with the ICC data from FIG. 7A. In particular, the addition of TGF-β1 induced a six-fold increase in αSMA transcripts, and the knockdown of IL1β provided a significant decrease in differentiation. The combined knockdown of IL1β and CDH11 lead to a greater attenuation of αSMA mRNA expression than IL1β knockdown alone, although the αSMA levels were still higher than the 'no TGF-β1' control. CDH11 knockdown resulted in a minor, but statistically significant, reduction of αSMA transcript levels relative to cells not treated with siRNA. Despite slight differences, the measurements of αSMA mRNA (3 days) and αSMA protein expression (4 days) post-transfection, respectively, were in agreement.

Figure 8:
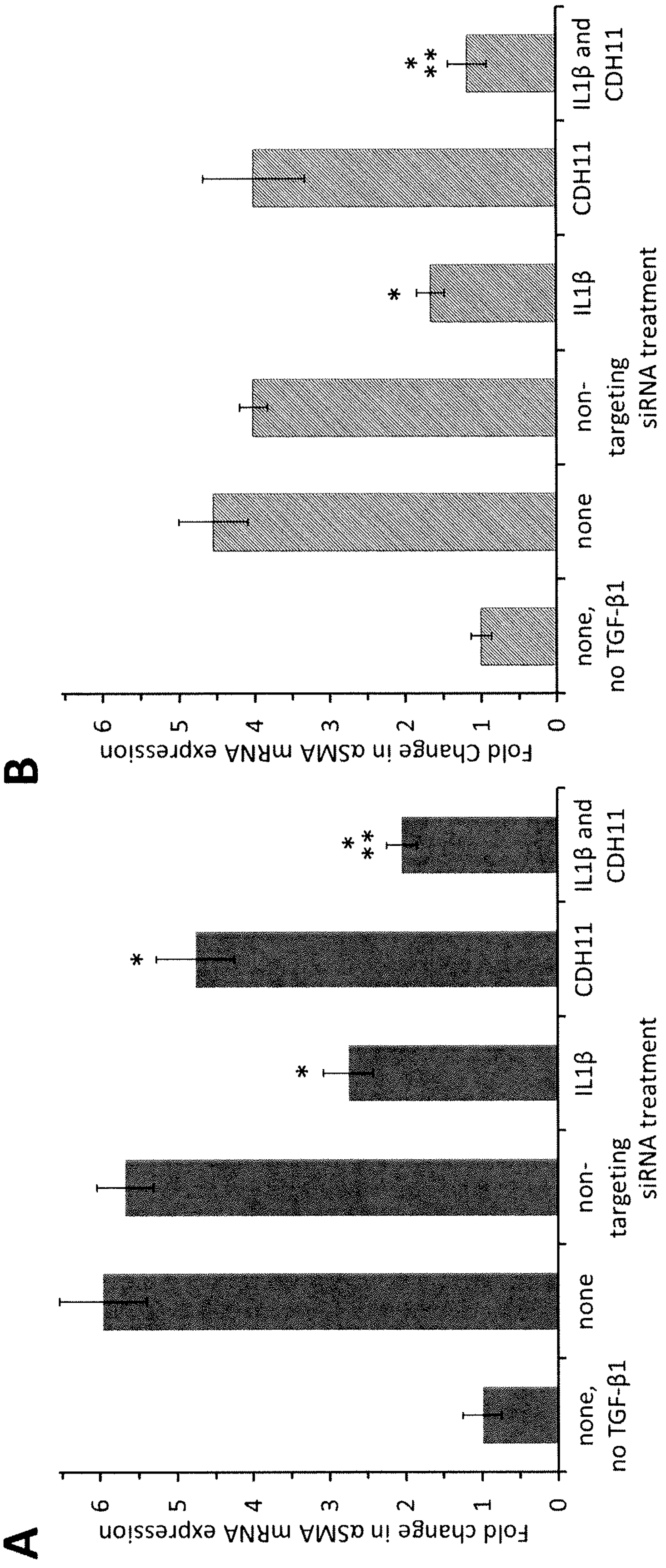
FIG. 8 shows attenuation of myofibroblast differentiation (αSMA mRNA expression) following two different siRNA dosing schedules. AoAFs underwent transfection at either t=0 h (A) or t=0 h and t=72 h (B) with various siRNA formulations and were treated with either 0 or 10 ng $mL^{-1}$ TGF-β1 to induce differentiation. (A) qPCR analyses of αSMA mRNA expression levels 3 days post-transfection in the single dose regimen. (B) qPCR analyses of αSMA mRNA expression levels 7 days after the first transfection (4 days after the second transfection) in the double dose regimen. qPCR values were normalized to the levels in the no siRNA and no TGF-β1 treatment control for each dosing schedule. All results are shown as the mean±standard deviation of data obtained from three independent samples. A single asterisk indicates a statistically significant difference in αSMA mRNA expression in comparison to the no siRNA and 10 ng $mL^{-1}$ TGF-β1 treatment control, and a double asterisk indicates a statistically significant difference in αSMA mRNA expression in comparison to the IL1β siRNA treatment formulation ($p<0.05$).
Figure 9:
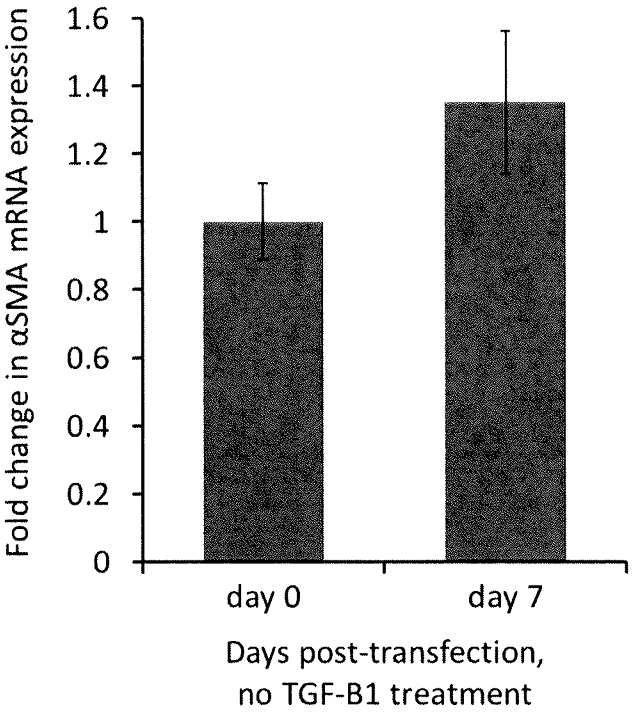
FIG. 9 shows changes in alpha smooth muscle actin (αSMA) mRNA expression (marker of myofibroblast differentiation) over the course of one week without transforming growth factor beta 1 (TGF-β1) treatment. qPCR analyses compared the αSMA mRNA expression levels on day 7 relative to day 0. Results are shown as the mean±standard deviation of data obtained from three independent samples. The samples were not significantly different from each other at a significance level of 0.05. The αSMA mRNA expression levels in AoAFs did not significantly change over the course of one week (significance level of 0.05). This suggests that the AoAFs primarily maintained their fibroblast phenotype over 7 days when seeded on tissue culture plastic.

The αSMA transcript levels also were studied on day 7 of the double dosing schedule. AoAFs incubated in TGF-β1 exhibited ~4.5 times more αSMA mRNA transcripts than untreated cells (FIG. 8B), suggesting that untreated cells did not significantly alter their fibroblast phenotype on tissue culture plastic over 7 days (FIG. 9). The delivery of IL1β siRNA significantly reduced αSMA mRNA levels relative to the delivery of non-targeting siRNA, whereas CDH11 silencing did not provide these effects. However, the combined knockdown of IL1β and CDH11 attenuated αSMA mRNA expression to the same level as the no TGF-β1 control, indicating that differentiation was completely halted over one week with the double dosing schedule.

Given the lack of response from CDH11 silencing alone, the significantly enhanced attenuation of differentiation from the combined delivery of IL1β and CDH11 siRNA in comparison to IL1β siRNA alone (i.e., combined effects that were more than simply additive) suggests that the two genes may cooperate synergistically. Little is known about the direct relationship between IL1β and CDH11, but Yoshioka et al. (*J. Pharm. Pharmacol.* 2015, 67, 1075) recently reported that the knockdown of CDH11 reduced IL1β-induced proliferation by 42% in rheumatoid arthritis-derived synovial fibroblast cells. Yoshioka et al. concluded that CDH11 is involved in IL1β-mediated pathways, and that there is an indirect interplay between the two genes via β-catenin. In a related study, Chang and coworkers (*Proc. Natl. Acad. Sci. U.S.A.* 2011, 108, 8402) demonstrated that CDH11 engagement has strong synergies with IL1β signaling upon interleukin 6 (IL-6) induction in synovial fibroblasts, and that the mitogen-activated protein kinase (MAPK) [c-Jun N-terminal kinase (JNK) and extracellular signal-regulated kinase 1 and 2 (ERK1/2)] and the nuclear factor kappa-light-chain-enhancer of activated B cells (NF-κB) pathways were activated. Thus, the signaling cascades of IL1β and CDH11 may be related through β-catenin, MAPK, and/or NF-κB in AoAFs. These reports suggest that the two genes affect one another in other cell types, but more work is needed to probe the intricate interactions between the downstream effectors of IL1β and CDH11 in AoAFs. However, our data strongly suggest that the combined knockdown of the two genes provides a powerful synergistic method for attenuating TGF-β1-induced myofibroblast differentiation.

2.7 Attenuation of Cellular Proliferation Following Gene Silencing

Figure 10:
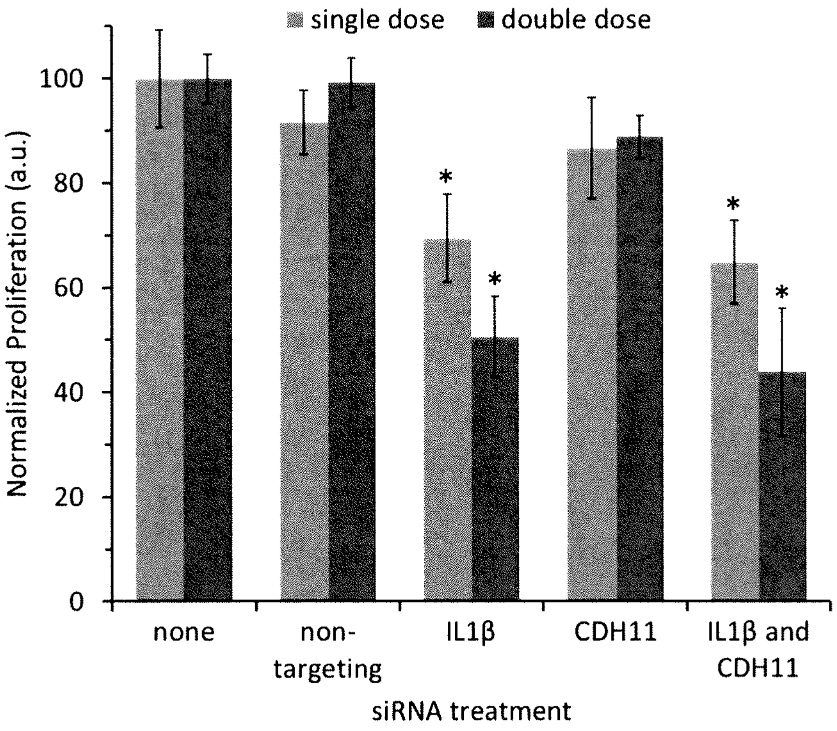
FIG. 10 shows proliferation of AoAFs following a single or double dose siRNA regimen. AoAFs were treated with different siRNA formulations and irradiated with 365 nm light for 10 min after each transfection. The change in the number of cells was measured using the AlamarBlue assay 4 days or 7 days after the first transfection for the single dose (light bars) and double dose (dark bars) experiments, respectively. Data represent the normalized extents of cellular proliferation relative to cells that were not treated with siRNA, with 100 indicating no change relative to untreated cells. A value of 0 indicates no change in the absolute number of cells from the time of transfection. Results are shown as the mean±standard deviation of data obtained from three independent experiments. An asterisk indicates a statistically significant difference in proliferation in comparison to the no siRNA treatment controls ($p<0.05$).

In addition to myofibroblast differentiation, increased cellular proliferation is a classic hallmark of fibrosis. The reduction of fibroblast proliferation is a critical therapeutic goal to mitigate maladaptive responses and promote healing in cardiovascular tissues, particularly in the first week following vessel injury. Changes in the growth rates of the AoAFs were analyzed to determine if the knockdown of IL1β and/or CDH11 affected proliferation. As shown in FIG. 10, non-targeting siRNA did not significantly alter proliferation, which is indicative of the biocompatibility of the hybrid nanocomplexes. The knockdown of IL1β reduced proliferation by ~30% and ~50% following a single and double dose, respectively. The delivery of only CDH11 siRNA provided a relatively minor reduction in proliferation rate in comparison to the untreated control samples. The combined knockdown of IL1β and CDH11 reduced proliferation to the same extent as IL1β alone. Thus, IL1β, but not CDH11, appears to play a critical role in AoAF proliferation.

Our findings in AoAFs are generally in agreement with most literature reports of IL1β and CDH11 in other cell types. While IL1β has been widely identified as playing a key role in fibroblast proliferation, few studies have implicated CDH11. For example, Vesey et al. (*J. Lab. Clin. Med.* 2002, 140, 342) found that IL1β was a potent inducer of proliferation with similar activities to those of TGF-β1 in human cortical fibroblasts. Consistent with these findings, our studies indicated that the synergistic effects of knocking down IL1β and CDH11 attenuated differentiation (FIG. 8) but were not detected in the AoAF proliferation analyses.

2.8 Cell Density Effects on CDH11 Knockdown

In both the single dose and double dose studies, the knockdown of CDH11 provided only minor, if any, attenuation of myofibroblast differentiation. However, previous work identified CDH11 upregulation in inflamed AoAFs as a primary marker of myofibroblasts, thus making it a promising target for mitigating differentiation. One possible reason for this discrepancy is that CDH11 signaling requires cell-cell adhesion, which occurs at high cell densities, yet under standard culturing conditions, cell-cell contacts are not made until confluency (3-4 d in our study). Within the context of FIG. 6B, CDH11 may be a better target after day 3 when the cells are beginning to become more confluent. A second possible explanation is that CDH11 is simply a downstream effector of other proteins that govern the differentiation pathway, and the modulation of CDH11 does not impact upstream cascades.

Figure 11:
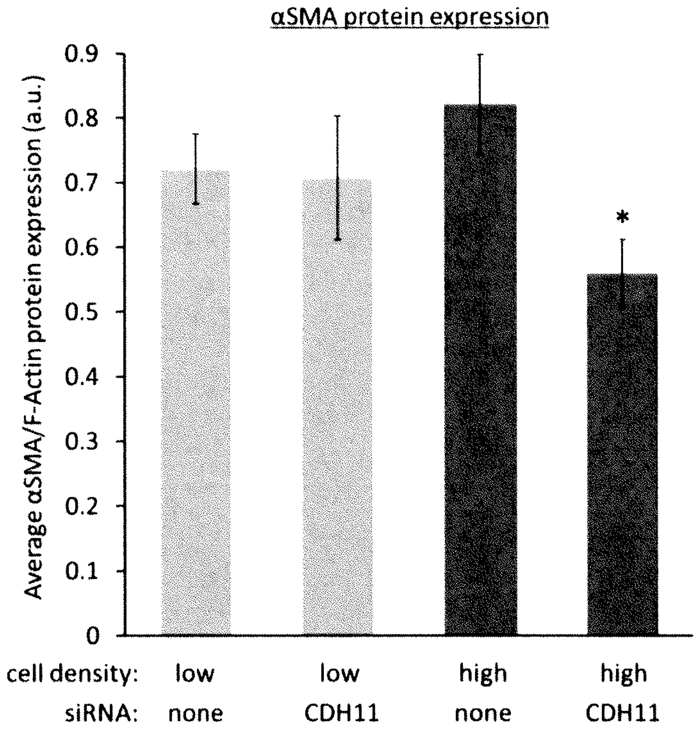
FIG. 11 shows effect of cell density on myofibroblast differentiation following CDH11 knockdown. AoAFs were plated at 10,000 cells $cm^{-2}$ (low density) or 30,000 cells $cm^{-2}$ (high density), transfected with CDH11 siRNA, and treated with 10 ng $mL^{-1}$ TGF-β1 to induce differentiation. ICC analyses were conducted to measure αSMA protein expression, and αSMA protein expression was quantified from ICC analyses. The average total fluorescence intensity of αSMA relative to F-actin of at least 100 cells per sample was measured using ImageJ. Results are shown as the mean±standard deviation of data obtained from three independent samples. An asterisk indicates a statistically significant difference in αSMA protein expression in comparison to the no siRNA treatment control at the appropriate cell density ($p<0.05$).

To determine if silencing CDH11 has a significant impact on differentiation under other culturing conditions, cells were grown at different confluencies. CDH11 siRNA was applied to low density and high-density cells. There were almost no AoAFs with cell-cell contacts in the low-density samples, but the majority of cells were in contact with other cells in the high-density samples. AoAFs growing at the higher density expressed greater amounts of CDH11, as reported in the literature. Both the low-density and high-density samples exhibited nearly complete knockdown when treated with CDH11 siRNA, despite the overexpression of CDH11 in the high-density case. The αSMA protein expression of the cells was measured, and there was no difference in αSMA protein levels between the untreated samples and treated low-density samples (FIG. 11). However, CDH11 siRNA treatment of the cells grown at high density was found to significantly reduce αSMA protein expression (FIG. 11), albeit to a lesser extent than IL1β siRNA treatment (see also FIGS. 7 and 8). Therefore, CDH11 knockdown is a more promising strategy for attenuating differentiation when the number of AoAF cell-cell contacts is greater.

This finding is particularly important because the in vivo environment of the adventitium is crowded, and the cells are densely packed with many cell-cell interactions. Recent reports in the literature also found CDH11 to be not merely a downstream effector of TGF-β1, but also a factor able to regulate myofibroblast differentiation through multiple other pathways. Moreover, the possible synergistic effects of CDH11 and IL1β knockdown (see FIG. 8B) and the role of CDH11 in the propagation vs. suppression of maladaptive responses in adventitial fibroblasts (e.g., by coordinating the contraction of fibroblast populations) justify further exploration of CDH11 as a possible therapeutic target. Taken together, CDH11 silencing may be a more promising strategy in clinical settings, especially if combined with the knockdown of IL1β.

3. Conclusion

We developed a novel lipid-polymer hybrid formulation to spatiotemporally control the knockdown of key genes implicated in maladaptive responses of human primary adventitial fibroblasts. Our nanocarriers remained dormant in AoAFs until triggered and then silenced protein expression to ≤5% of initial levels upon application of a photo stimulus. Additionally, the dynamics of protein turnover of two functional genes, IL1β and CDH11, were accurately predicted using simple kinetic modeling. This approach allowed the implementation of a double dosing regimen that sustained the knockdown of both genes for one week, which is the time period relevant for severely injured tissue to undergo adventitial remodeling. Cells with silenced IL1β expression for one week exhibited attenuated differentiation and a ~50% reduction in proliferation. The effects of CDH11 knockdown alone were relatively minor, but were significantly enhanced at higher cell densities. However, the combined delivery of IL1β and CDH11 siRNAs resulted in the complete halting of myofibroblast differentiation, as characterized by αSMA expression. Thus, this work provides a new formulation design for imparting stimuli-responsive features into materials capable of transfecting primary cells and elucidated the key functional roles of IL1β and CDH11 in mediating fibrotic responses in AoAFs, both of which are critical for advancing therapies in the clinic to treat cardiovascular disease.

4. Experimental Section 4.1 Materials

LIPOFECTAMINE RNAiMAX, anti-CDH11 siRNA, and rabbit IgG polyclonal antibody were purchased from Life Technologies (Carlsbad, CA). Non-targeted (universal negative control) siRNAs were purchased from Sigma-Aldrich (St. Louis, MO). Anti-IL1β siRNA and rabbit IgG polyclonal antibody were obtained from Santa Cruz Biotechnology (Dallas, TX). PAA ($M_w$=240,000 g mol$^{-1}$) was obtained from Acros Organics (Waltham, MA). The mPEG-b-P(APNBMA)$_n$ polymers ($M_n$=7,900 g mol$^{-1}$, n=7.9; $M_n$=13,100 g mol$^{-1}$, n=23.6) were synthesized via atom-transfer radical polymerization as described previously (*Polym. Chem.* 2014, 5, 5535). Dulbecco's Modified Eagle Medium (DMEM) and Dulbecco's phosphate-buffered saline (DPBS, 150 mM NaCl, pH of 7.4) were obtained from Corning Life Sciences—Mediatech Inc. (Manassas, VA). Opti-MEM medium, SuperSignal West Dura Chemiluminescent Substrate, Phalloidin-660, Hoescht 33258, TRIzol Reagent, and AlamarBlue were purchased from Life Technologies (Carlsbad, CA). Antibodies (rabbit anti-GAPDH IgG polyclonal, rabbit anti-αSMA IgG polyclonal, secondary goat anti-rabbit IgG polyclonal-horseradish peroxidase (HRP), and secondary goat anti-rabbit IgG polyclonal-Alexa Fluor 488) and recombinant human TGF-131 were purchased from AbCam (Cambridge, MA). Bovine serum albumin (BSA) and a bicinchoninic acid (BCA) protein assay kit were purchased from Pierce (Rockford, IL). Primers were obtained from Eurofins MWG Operon (Huntsville, AL) with the following sequences: αSMA forward 5' TATCCCCGGGACTAAGACGG 3' (SEQ ID NO: 1); αSMA reverse 5' CACCATCACCCCCTGATGTC 3' (SEQ ID NO: 2); GAPDH forward 5' CGGGTTCC-TATAAATACGGACTGC 3' (SEQ ID NO: 3); GAPDH reverse 5' CCCAATACGGCCAAATCCGT 3'(SEQ ID NO: 4). The iTaq Universal SYBR Green One-Step Kit and optical flat 8-cap strips were purchased from Bio-Rad (Hercules, CA). All other reagents were obtained from Thermo Fisher Scientific (Waltham, MA).

4.2 Formulation and Characterization of siRNA Nanocomplexes

The hybrid nanocomplexes were formed using a solution mixing self-assembly method. Solutions of siRNA and LIPOFECTAMINE RNAiMAX were prepared in Opti-MEM and mixed according to Life Technologies' protocol (to produce a final solution containing 0.2 μg siRNA and 3 μL LIPOFECTAMINE in a total volume of 96 μL). After a 5 min incubation period, 0.2 μg 240,000 g mol$^{-1}$ PAA was added to the lipoplex solution. The solution was mixed via gentle vortexing and then incubated for 20 min. A separate polymer solution was prepared by adding equimolar amounts of mPEG-b-P(APNBMA)$_{7.9}$ and mPEG-b-P(APNBMA)$_{23.6}$, on the basis of cationic amine groups. The polymer solution was mixed, via gentle vortexing, with the lipoplex/PAA solution to form hybrid complexes with an N:P ratio (N: cationic amine groups on polymer, P: anionic phosphate groups on siRNA) of 4. The hybrid complexes were incubated in a dark environment at room temperature for 30 min prior to further analysis. For the on/off photo-controlled protein silencing experiments, two separate control formulations were used: lipoplexes made with LIPOFECTAMINE RNAiMAX according to the manufacturer's protocol and polyplexes formed as described previously (Vol. 50, Acta Biomater. 2017, 407).

The average nanocomplex diameters were determined using fluorescence correlation spectroscopy (FCS). The average zeta potentials were determined using a Brookhaven Instruments (Brookhaven, CT) ZetaPALS, and each sample was measured with 3 runs of 10 cycles. Nanocomplexes were formulated with Dy547-labeled small interfering RNA (siRNA) and analyzed on cover slips. FCS measurements were carried out on an LSM 780 confocal microscope (Carl Zeiss, Oberkochen, Germany) using a 561 nm laser and a 40× (numerical aperture=1.2) water immersion apochromat objective. Thirty measurements, each lasting 8 s, were taken for each sample, and data analysis was performed with ZEN 2010 software (Carl Zeiss). A solution of free Alexa Fluor 555 dye, with an assumed diffusion coefficient of 340 μm$^2$ s$^{-1}$,[2] was used to determine the structural and measurement parameters. Results are reported as the mean and standard deviation of data obtained from three independent experiments.

siRNA release from the hybrid nanocomplexes was measured by gel electrophoresis. The hybrid nanocomplexes were formulated, incubated in SDS for 30 min, and subjected to gel electrophoresis. Gels were prepared with 4 wt % agarose and stained with 0.5 μg $mL^{-1}$ ethidium bromide. For analysis, 37.5 μL of polyplex solution was added to 7.5 μL of loading dye (3:7 (v/v) glycerol/water) before being added to the wells of the gel. Gels were run at 100 V for 30 min and imaged using a Bio-Rad Gel Doc XR (Hercules, CA). ImageJ software (National Institutes of Health, Bethesda, MD) was used to quantify the amounts of free siRNA by analyzing band intensities.

4.3 Cell Culture

Human aortic adventitial fibroblasts were obtained from Lonza (Walkersville, MD) and cultured following Lonza's protocol in stromal cell basal medium (SCBM) supplemented with the stromal cell growth medium (SCGM) SingleQuot Kit. The cells were cultured in a humid environment maintained at 37° C. and 5 vol % $CO_2$.

4.4 In Vitro Cell Transfection and Cell Viability Analysis

AoAFs were cultured in plates at a density of 15,000 cells $cm^{-2}$ for 24 h. Before transfection, the supplemented growth medium was removed, the cells were washed with DPBS, and Opti-MEM was added to the plates. The nanocomplex solutions were then added dropwise at a final siRNA concentration of 10 nM. Following a 3 h transfection period, the Opti-MEM was replaced with supplemented growth medium for a 30 min recovery period. The medium was replaced with phenol red-free Opti-MEM, and the cells were irradiated with 365 nm light at an intensity of 200 W $m^{-2}$ for 10 min on a 37° C. hotplate. Supplemented growth medium was added to the wells after irradiation. To stimulate cell differentiation in some samples, TGF-β1 was added to the growth medium at a concentration of 10 ng $mL^{-1}$. The growth medium and TGF-β1 were replenished every two days.

For cell viability analyses, AoAF cells were seeded into six-well plates at a density of 15,000 cells $cm^{-2}$ and allowed to adhere for 24 h prior to toxicity analyses. After 48 h, AB was added directly into the culture medium to a final concentration of 10 vol %, and the cells were incubated for 6 h at 37° C., 5 vol % $CO_2$. Fluorescence was measured using a GloMax-multi detection system plate reader (Promega, Madison, WI). To determine the baseline fluorescence, medium containing 10 vol % AB was added to a well without cells.

4.5 Protein Knockdown Analysis

Figure 12:
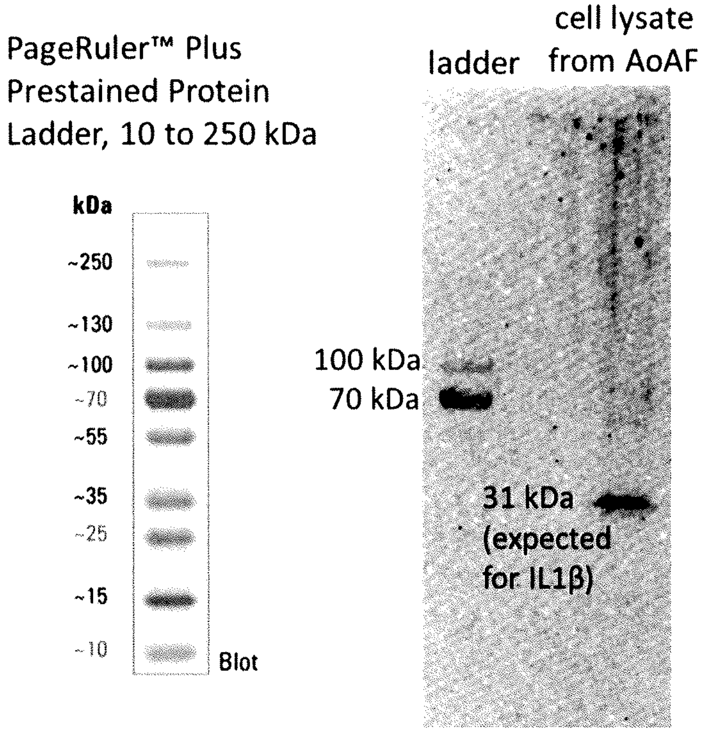
FIG. 12 shows representative example of western blot staining for the precursor interleukin 1 beta (IL1β) protein [~31 kDa] from the cell lysate of AoAFs. Solutions of PageRuler™ Plus Prestained Protein Ladder (10 kDa to 250 kDa) [Thermo Fisher Scientific (Waltham, MA)] and AoAF cell lysate were subjected to 4%-20% SDS-polyacrylamide gel electrophoresis (SDS-PAGE). The anti-IL1β rabbit IgG polyclonal antibody specifically stained only one band in the AoAF cell lysate. The targeted protein had a molecular weight of ~31 kDa, which was the expected molecular weight for the precursor of IL1β.

Western blot analyses were used to measure IL1β and CDH11 protein silencing in AoAFs. In the single dose experiments, cells were transfected and lysed at the specified time points. The protein was extracted from the cells by adding a lysis solution composed of 0.5 vol % Triton X-100, 0.5% sodium deoxycholate, 150 mM NaCl, 5 mM Tris-HCl (pH 7.4), 5 mM EDTA, and 1× Halt Protease and Phosphatase Inhibitor cocktail. For the repeated dosing experiments, a second transfection of nanocomplexes was performed 72 h after the first transfection, and protein was extracted at the given time points. The total protein concentration of each sample was measured using the BCA Protein Assay Kit. The protein solutions were subjected to 4%-20% sodium dodecyl sulfate polyacrylamide gel electrophoresis (SDS-PAGE) for 35 min at 150 V. The separated proteins then were transferred onto a poly(vinylidene fluoride) membrane at 18 V for 75 min. The membrane was subsequently blocked in 5 vol % BSA in Tris-HCl-buffered saline (50 mM Tris-HCl, pH 7.4, 150 mM NaCl) containing 0.1 vol % Tween 20 (TBST) at room temperature for 1 h. The membrane was incubated overnight with IL1β or CDH11 primary antibodies in TBST at 4° C. The next day, the membrane was incubated in a solution of secondary antibody conjugated to HRP for 1 h. The SuperSignal West Dura Chemiluminescent Substrate was used to enable detection of the bands through chemiluminescent imaging in a FluorChem Q (ProteinSimple, San Jose, CA). To image the GAPDH bands, the membrane was stripped for 15 min with Restore PLUS Western Blot stripping buffer, blocked in BSA solution for 1 h, and subsequently incubated with GAPDH primary antibody overnight. The next day, after incubation in a solution of secondary goat anti-rabbit antibody conjugated to HRP, chemiluminescent imaging was used to detect the bands. The intensity of each target protein was analyzed with ImageJ software. Note: A representative western blot image of the anti-IL1β antibody staining is located in FIG. 12.

4.6 RNAi Modeling

A set of equations (Equations 1-3) was solved using differential equation solver ode45 in MATLAB (*ACS Biomater. Sci. Eng.* 2016, 2, 1582).

$$\frac{d[\text{mRNA}]}{dt} = k_{mRNA}[\text{DNA}] - k_{m,deg}[\text{mRNA}] - k_{siRNA}[\text{siRNA}] \quad (1)$$

$$\frac{d[\text{protein}]}{dt} = k_{prot}[\text{mRNA}] - k_{p,deg}[\text{protein}] \quad (2)$$

$$\frac{d[\text{siRNA}]}{dt} = -k_{s,deg}[\text{siRNA}] \quad (3)$$

Equations S1-3. The system of ordinary differential equations used to model the changes in concentrations of mRNA, protein, and siRNA for each gene (IL1β and CDH11) separately. $k_{mRNA}$, $k_{siRNA}$, and $k_{prot}$ are the rate constants for the production of mRNA, siRNA, and protein, respectively. $k_{m,deg}$, $k_{s,deg}$, and $k_{p,deg}$ are the rate constants for the degradation of mRNA, siRNA, and protein, respectively. The degradation rate constants were computed on the basis of experimentally-determined cell doubling times (see FIG. 12) and component half-lives reported in literature, and the production rate constants were fit to ensure mRNA and protein steady-state values were reached in the absence of siRNA.

Figure 13:
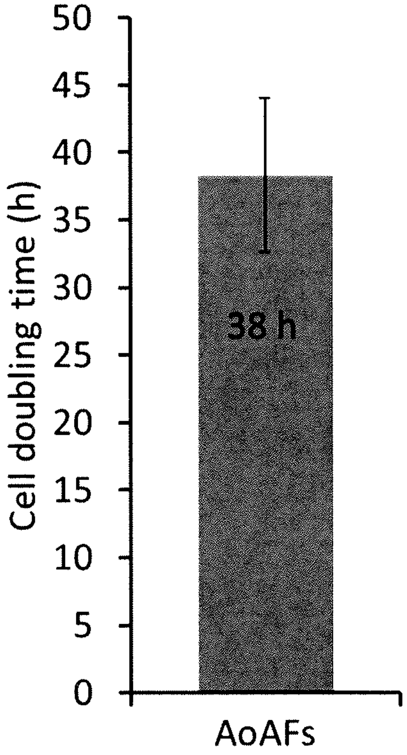
FIG. 13 shows cell doubling time of AoAFs, as evaluated by the AlamarBlue assay. Results are reported as the mean±standard deviation of data obtained from three independent samples. The AoAFs had a doubling time of ~38 h, which was incorporated into the $k_{s,deg}$ rate constant estimate for the kinetic modeling predications.

Each siRNA dose was modeled by increasing the normalized siRNA concentration by 100 units following time points corresponding to light-triggered siRNA release. The siRNA turnover rate was estimated by determining the cell doubling time of AoAFs cultured in standard growth medium, which was measured to be ~38 h (FIG. 13). Protein degradation rate constants were computed on the basis of IL1β and CDH11 half-lives, which were ~2.5 h and ~8 h, respectively, as reported in the literature. The mRNA degradation rate constants were estimated by using a ~8 h half-life for both genes, as this is the approximate average mRNA turnover rate.

4.7 Immunocytochemistry

AoAF cells were transfected with siRNAs. At the specified time points, the cells were washed with DPBS and fixed in 4% paraformaldehyde for 15 min. The cells were permeabilized with 0.1% (v/v) Triton X-100 in DPBS for 15 min and blocked with 5% bovine serum albumin in DPBS for 1 h. αSMA, a marker of myofibroblast differentiation, was detected by overnight incubation at 4° C. in an αSMA primary antibody solution [2 μg $mL^{-1}$ in DPBS]. Alternatively, CDH11 protein expression was detected by overnight incubation at 4° C. in a CDH11 primary antibody solution [2 μg $mL^{-1}$ in DPBS]. Samples were then incubated with a solution of secondary antibody labeled with AlexaFluor® 488 [4 μg $mL^{-1}$ in DPBS] for 1 h. Cells were incubated in a solution of Phalloidin-660 [160 nM in DPBS] for 30 min to detect F-actin, and then the cells were incubated in a solution of Hoescht 33258 [0.5 μg $mL^{-1}$ in DPBS] for 10 min to detect nuclear DNA. Cells were visualized using a 20× objective on an LSM META 510 confocal microscope (Zeiss, Germany) controlled by Image Pro Plus software (version 7.0; Media Cybernetics). The fluorescence intensities in zoomed-out (4× magnification) micrographs were quantified using Image) software. The fluorescence intensities of at least 1,000 cells from each channel were averaged through the quantification of total pixel intensity. Then, the signal from the protein of interest (αSMA or CDH11) was divided by the signal from the housekeeping protein (F-actin).

4.8 mRNA Knockdown Analysis

αSMA mRNA knockdown was measured using quantitative PCR (qPCR). For analyses in AoAFs, single and double transfections were carried out, and RNA was isolated by TRIzol Reagent according to the manufacturer's protocols. The iTaq Universal SYBR Green One-Step Kit was used to prepare samples for qPCR in triplicate, using the αSMA or GAPDH primers, as described in the manufacturer's protocols. cDNA synthesis and qPCR were conducted on a Bio-Rad CFX96™ using the following conditions: 10 min at 50° C.; 1 min at 95° C.; 40 cycles of 10 s at 95° C. and 30 s at 60° C.; and finally, a 65° C. to 95° C. ramp at a rate of 0.5° C. every 5 s. The $\Delta\Delta C_T$ method was used for analysis, and all sample data were normalized to data from untreated cell controls.

To study mRNA knockdown in vein fibroblasts and aortic fibroblasts (Cell Biologics, Chicago, IL), cells were incubated with hybrid lipid-polymer nanocomplexes or Lipofectamine RNAiMAX lipoplexes for 3 h and irradiated with 365 nm light for 10 min. IL1β mRNA knockdown was measured using qPCR after 24 h of culture subsequent to transfection. RNA was isolated by TRIzol Reagent (Life Technologies, Carlsbad, CA) according to the manufacturer's protocols. The iTaq Universal SYBR Green One-Step Kit (Bio-Rad, Hercules, CA) was used to prepare samples for qPCR in triplicate, using αSMA or glyceraldehyde 3-phosphate dehydrogenase (GAPDH) primers, as described in the manufacturer's protocols. cDNA synthesis and qPCR were conducted on a Bio-Rad CFX96™ using the following conditions: 10 min at 50° C.; 1 min at 95° C.; 40 cycles of 10 s at 95° C. and 30 s at 60° C.; and finally, a 65° C. to 95° C. ramp at a rate of 0.5° C. every 5 s. The ΔΔCT method was used for analysis,[1] and all sample data were normalized to data from untreated cell controls irradiated with 365 nm for 10 min.

4.9 Cell Proliferation

Cell growth was evaluated using the AlamarBlue assay according to the manufacturer's protocols. Cells were transfected and grown in fully supplemented medium for 4 days or 7 days after the first transfection for the single dose and double dose experiments, respectively. Medium containing 10 vol % AlamarBlue was added to each well, and the cells were incubated for 6 h in a humid environment maintained at 37° C. and 5 vol % $CO_2$. Fluorescence was measured using a GloMax-multi detection system plate reader (Promega, Madison, WI). To determine the baseline fluorescence, medium containing 10 vol % AlamarBlue was added to a well without cells. Note: All samples were treated with the photo-stimulus to isolate the effects of protein knockdown on cellular proliferation.

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed:

1. A hybrid nanocomplex comprising at least one agent, at least one cationic polymer responsive to a stimulus, at least one anionic polymer, and at least one cationic lipid, wherein the at least one agent is complexed with the at least one cationic lipid to form a lipoplex, wherein the lipoplex is coated by the at least one anionic polymer, wherein the anionic polymer is coated by the cationic polymer, wherein the at least one agent is capable of being released from the hybrid nanocomplex in a human cell upon exposure to the stimulus, wherein at least one agent is a polynucleotide selected from the group consisting of small interfering RNA (siRNA), messenger RNA (mRNA), microRNA (miRNA), small hairpin RNA (shRNA), and combinations thereof, and wherein the released at least one agent is active in the human cell.

2. The hybrid nanocomplex of claim 1, wherein the at least one agent comprises at least one small interfering RNA (siRNA).

3. The hybrid nanocomplex of claim 1, wherein the stimulus is selected from the group consisting of light, pH, temperature, ultrasound, enzymes, redox potential, magnetic fields, electric fields, nucleic acids, hydrolysis, mechanical, and combinations thereof.

4. The hybrid nanocomplex of claim 1, wherein the stimulus is light, wherein the at least one cationic polymer comprises mPEG-b-poly(5-(3-(amino) propoxy)-2-nitrobenzyl methacrylate) [mPEG-b-P(APNBMA)], wherein mPEG is methoxy-poly(ethylene glycol).

5. The hybrid nanocomplex of claim 1, wherein the at least one anionic polymer is selected from the group consisting of poly(acrylic acid) (PAA), heparin, polyglutamic acid (γ-PGA), and polynucleotides.

6. The hybrid nanocomplex of claim 1, wherein the at least one cationic lipid is selected from the group consisting of N-[1-(2,3-dioleyloxy) propyl]-N,N,N-trimethylammonium chloride (DOTMA), 1,2-bis(oleoyloxy)-3-(trimethylammonio)propane (DOTAP), 2,3-dioleyloxy-N-[2(sperminecarboxamido)ethyl]-N, N-dimethyl-I-propanaminium, trifluoroacetate (DOSPA), dioleoylphosphatidylethanolamine (DOPE), dioleoylphosphatidylcholine (DOPC) and a combination thereof.

7. The hybrid nanocomplex of claim 1, wherein the at least one agent comprises at least one small interfering RNA (siRNA), wherein the stimulus is light, wherein the at least one cationic polymer consists of $mPEG-b-P(APNBMA))_{7.9}$, $MPEG-b-P(APNBMA))_{23.6}$ or a combination thereof, wherein mPEG is methoxy-poly(ethylene glycol), and wherein the at least one anionic polymer consists of poly (acrylic acid) (PAA) having a molecular weight (MW) of 250 kDa.

8. A composition comprising the hybrid nanocomplex of claim 1.

9. The composition of claim 8, wherein the at least one agent remains in the hybrid nanocomplex for at least one week in the absence of the stimulus.

10. A method of delivering at least one active agent into human cells, comprising (a) administering to the human cells the hybrid nanocomplex of claim 1, whereby the hybrid nanocomplex moves into the human cells, and wherein the at least one agent remains in the hybrid nanocomplex in the human cells until the human cells are exposed to the stimulus.

11. The method of claim 10, wherein the at least one agent remains in the hybrid nanocomplex in the human cells for at least one week in the absence of the stimulus.

12. The method of claim 10, further comprising (b) exposing the human cells to the stimulus, whereby the at least one agent is released from the hybrid nanocomplex, wherein the released at least one agent becomes active in the human cells.

13. The method of claim 12, further comprising repeating step (a) for at least once before step (b).

14. The method of claim 12, wherein the human cells express at least one protein, and wherein the at least one agent comprises at least one small interfering RNA (siRNA) against the at least one protein, further comprising reducing the expression of the at least one protein.

15. The method of claim 10, wherein the human cells are human primary cells.

16. The method of claim 10, wherein the human cells are from a subject.

17. The method of claim 10, wherein the human cells are in a subject.

18. The hybrid nanocomplex of claim 1, wherein the human cell is a human primary cell.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1

tatccccggg actaagacgg                                             20


<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2

caccatcacc ccctgatgtc                                             20


<210> SEQ ID NO 3
<211> LENGTH: 24
```

-continued

```
<212> TYPE: DNA
<213> ORGANISM: Artificial Sequence
<220> FEATURE:
<223> OTHER INFORMATION: Synthetic

<400> SEQUENCE: 3

cgggttccta taaatacgga ctgc                                   24


<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4

cccaatacgg ccaaatccgt                                        20
```